(12) United States Patent
Datta et al.

(10) Patent No.: US 8,734,814 B2
(45) Date of Patent: May 27, 2014

(54) RECOMBINANT MICROORGANISMS AND USES THEREOF

(76) Inventors: Asis Datta, New Delhi (IN); Sumit Ghosh, New Delhi (IN); Swagata Ghosh, New Delhi (IN); Hanumantha Rao Kongara, New Delhi (IN); Mohan Kamthan, New Delhi (IN)

(*) Notice: Subject to any disclaimer, the term of this patent is extended or adjusted under 35 U.S.C. 154(b) by 0 days.

(21) Appl. No.: 13/451,481

(22) Filed: Apr. 19, 2012

(65) Prior Publication Data

US 2013/0230557 A1    Sep. 5, 2013

(30) Foreign Application Priority Data

Mar. 2, 2012   (IN) .............................. 622/DEL/2012

(51) Int. Cl.
*A61K 39/106*    (2006.01)
*A61K 39/02*    (2006.01)

(52) U.S. Cl.
CPC ............ *A61K 39/107* (2013.01); *Y10S 435/909* (2013.01)
USPC ...................... 424/261.1; 435/252.1; 435/909

(58) Field of Classification Search
CPC .................................................. A61K 39/107
See application file for complete search history.

(56) References Cited

U.S. PATENT DOCUMENTS 6,248,329 B1 *   6/2001   Chandrashekar et al. . 424/191.1

OTHER PUBLICATIONS

The Dictionary of Immunology, Herbert et al eds, Academic Press, 1995, definition of vaccine.*
Feng et al (Infection and Immunity, 64(1):363-365, 1996).*
Ghosh et al (Molecular Microbiology, 80(6):1549-1560, published on line May 5, 2011).*
Chen et al., "Evaluation of N-acetylchitooligosaccharides as the main carbon sources for the growth of intestinal bacteria," *FEMS Microbiology Letters*, 209:53-56, (2002).
Homer et al., "Effects of N-Acetylglucosamine on Carbohydrate Fermentation by *Streptococcus mutans* NCTC 10449 and *Streptococcus sobrinus* SL-1," *Infection and Immunity*, 61(1):295-302, (1993).
Murad et al., "Clp10, an efficient and convenient integrating vector for *Candida albicans*," *Yeast*, 16:325-327, (2000).
Plumbridge et al., "DNA binding sites for the Mlc and NagC proteins: regulation of nagE, encoding the N-acetylglucosamine specific transporter in *Escherichia coil*," *Nucleic Acids Research*, 29(2):506-514, (2001).
Schmittgen et al., "Analyzing real-time PCR data by the comparative CT method," *Nature Protocols*, 3(6):1101-1108, (2008).
Singh et al., "Attenuation of Virulence and Changes in Morphology in *Candida albicans* by Disruption of the N-Acetylglucosamine Catabolic Pathway," *Infection and Immunity*, 69(12): 7898-7903, (2001).
Yamano et al., "Cloning and Sequencing of the Genes for N-Acetylglucosamine Use That Construct Divergent Operons (nagE-nagA C) from *Vibrio cholerae* Non-01," *Biosci. Biotech. Biochem.*, 61(8):1349-1353, (1997).

* cited by examiner

*Primary Examiner* — Patricia A Duffy
(74) *Attorney, Agent, or Firm* — Alston & Bird LLP

(57) ABSTRACT

The present invention relates to recombinant strains of *Vibrio* spp, which are unable to utilize the amino sugar N-acetylglucosamine (GlcNAc) as a sole carbon source. This inability to utilize GlcNAc severely impairs the colonization property of the recombinants. The present invention also provides compositions comprising these recombinant strains for use in pharmaceuticals and in providing immunity.

13 Claims, 6 Drawing Sheets

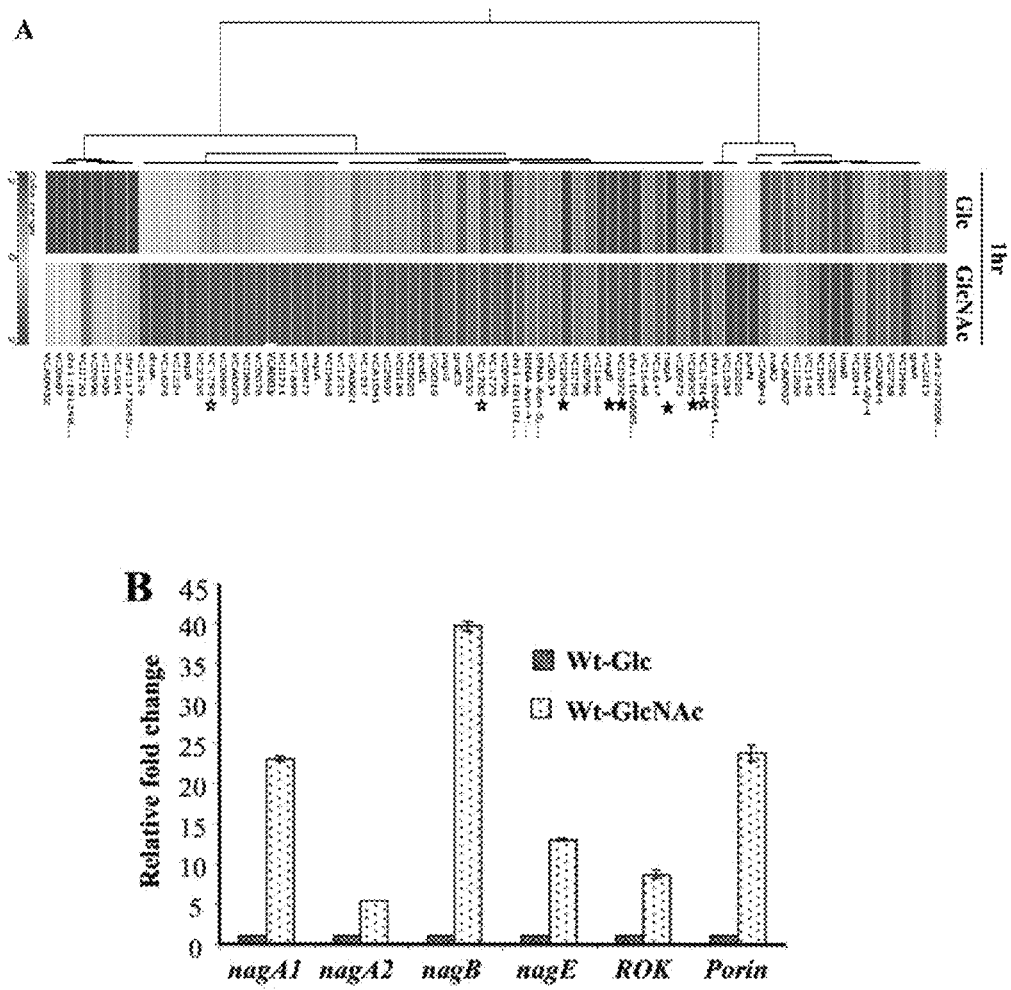
FIGURES 1A, B

A
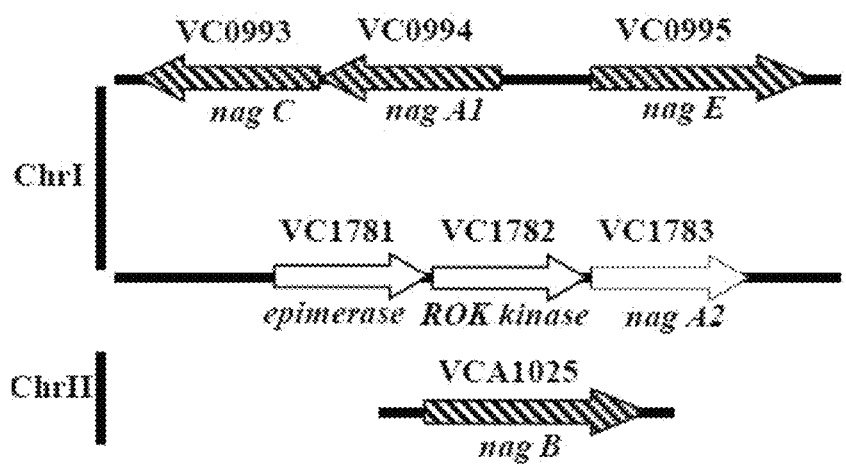
B
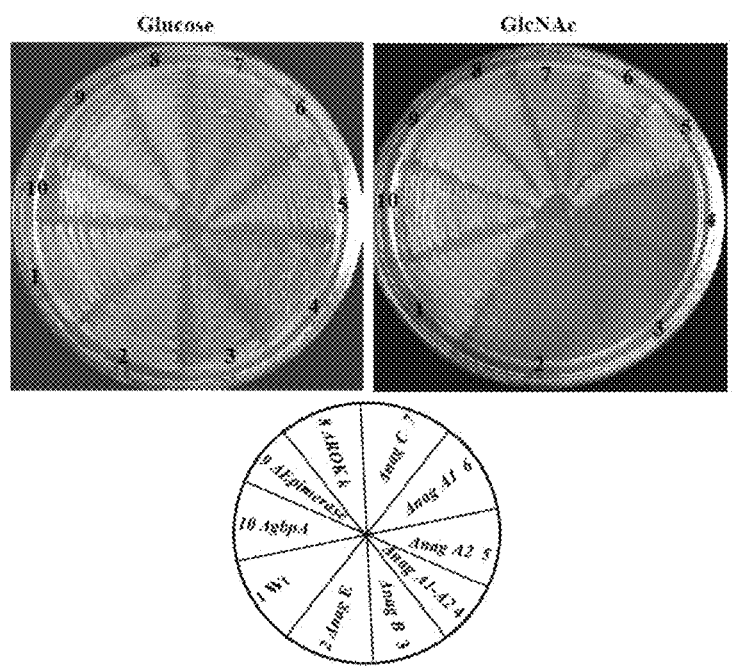
FIGURES 2A, B

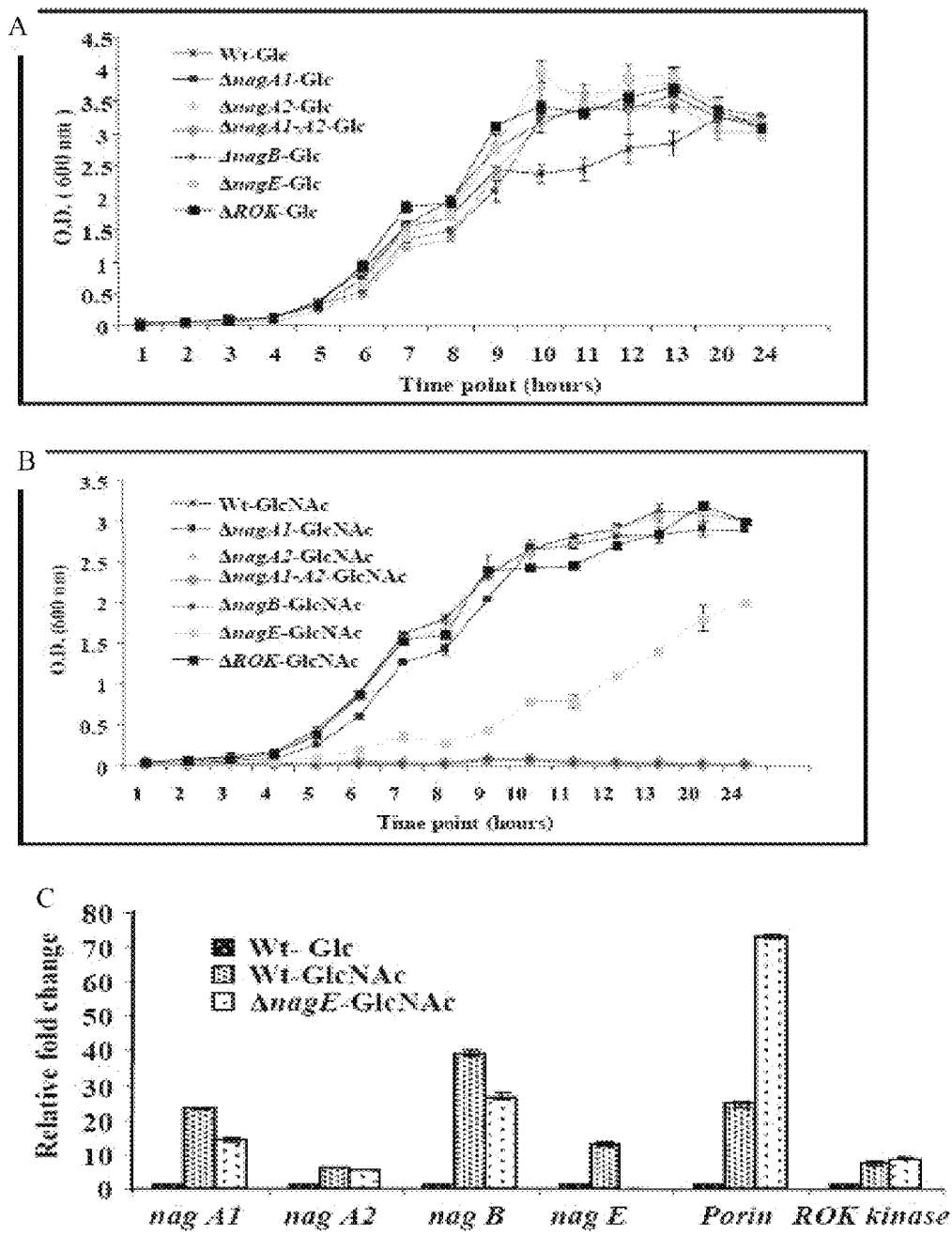
FIGURES 3A, B, C

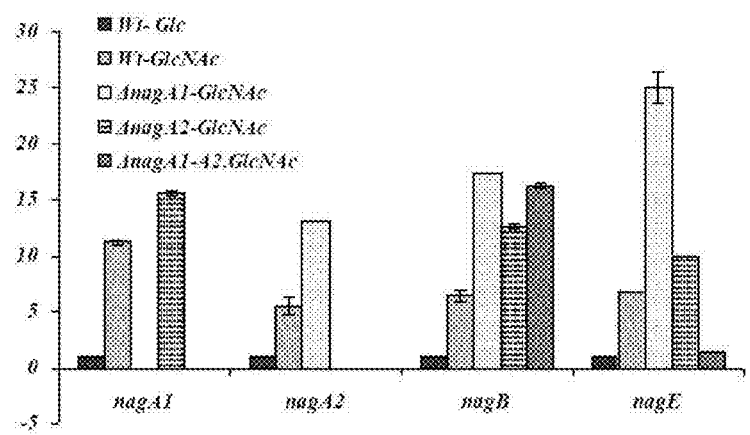
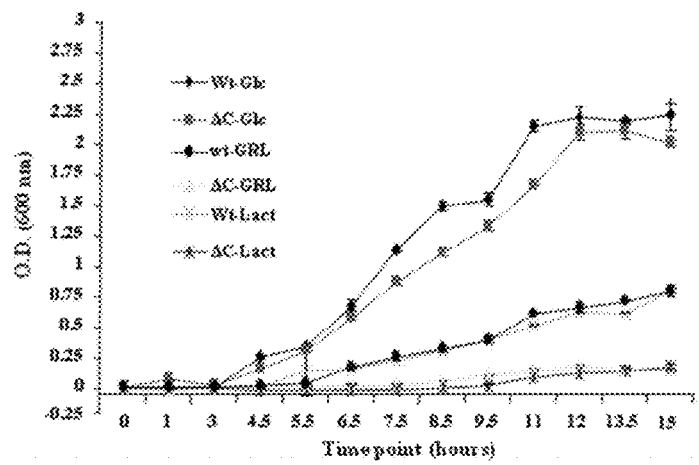
FIGURES 4A, B

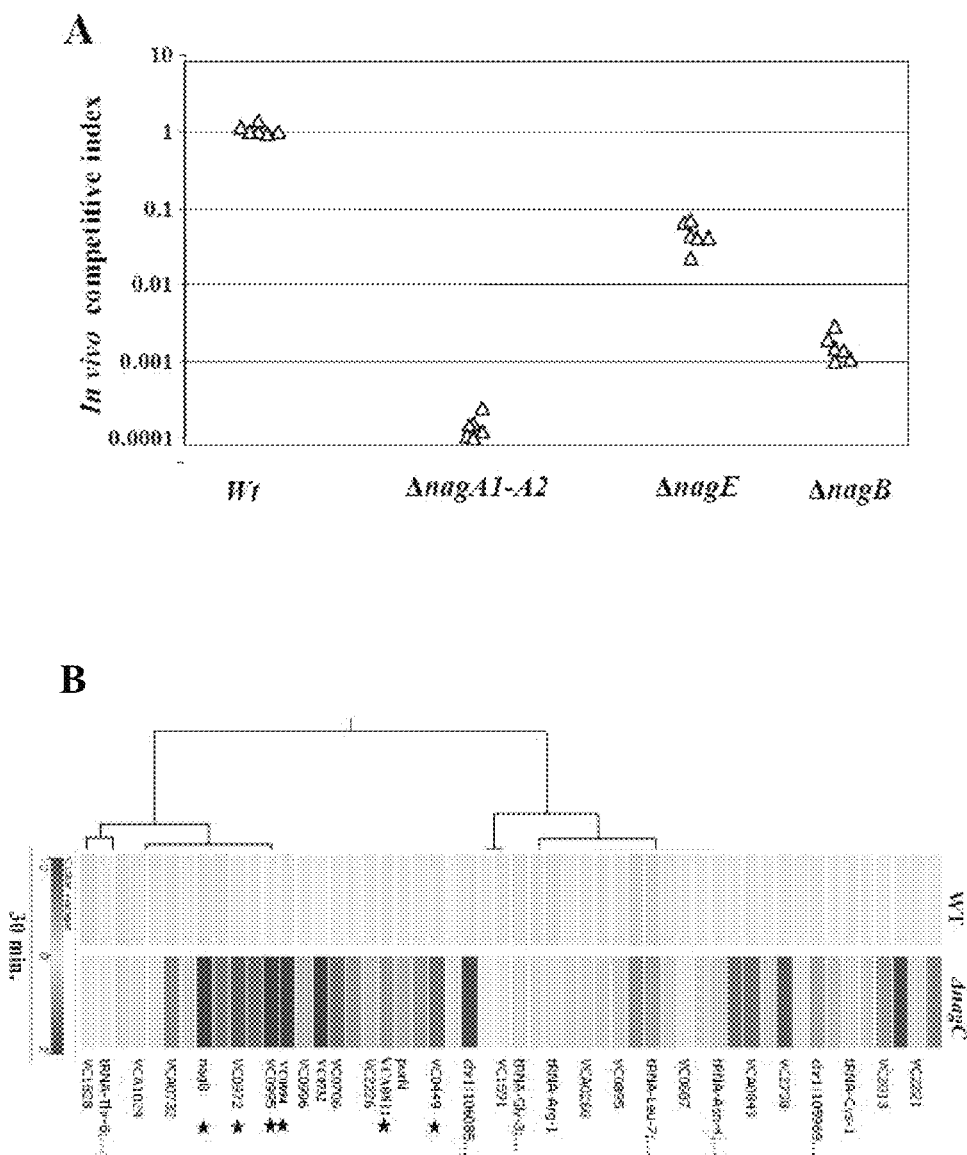
FIGURES 5A, B

A
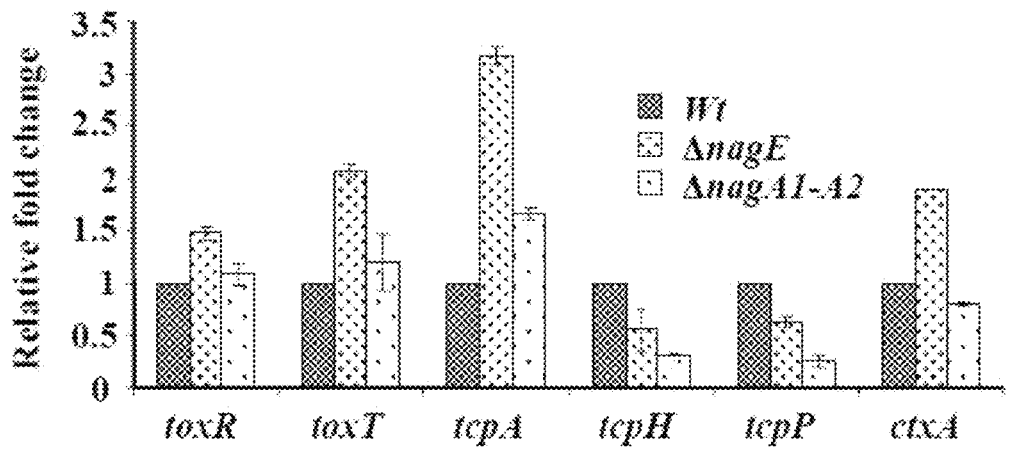
B
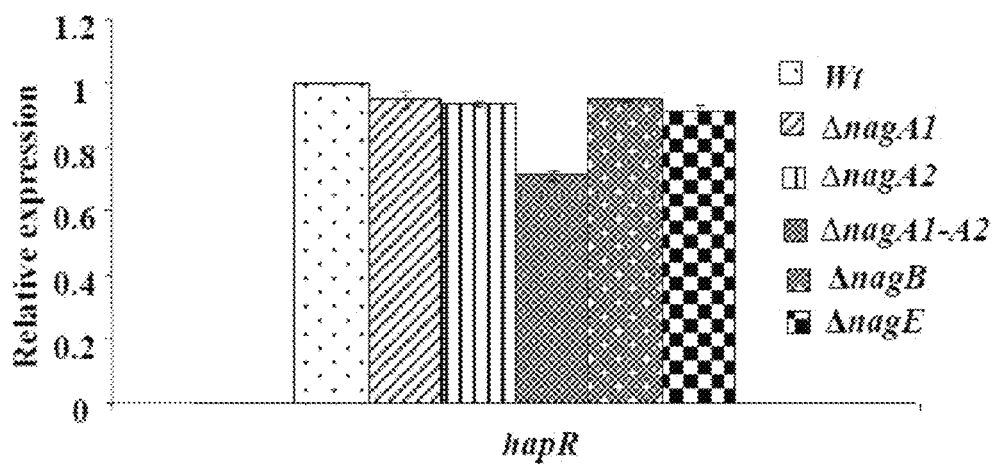
FIGURES 6A, B

RECOMBINANT MICROORGANISMS AND USES THEREOF

CROSS-REFERENCE TO RELATED APPLICATION

This application claims priority from Indian application 622/DEL/2012 filed Mar. 2, 2012, which is incorporated by reference in its entirety for all purposes.

REFERENCE TO SEQUENCE LISTING SUBMITTED IN COMPUTER READABLE FORM

The sequence listing in file 418531_SEQLST.txt was created Apr. 19, 2012 and is 5,573 bytes. This sequence listing is hereby incorporated by reference.

FIELD OF INVENTION

The present invention relates to recombinant strains of *Vibrio* spp., in particular, *Vibrio cholerae*. The recombinant strains of *V. cholerae* as disclosed in the present invention show an impaired ability of colonization. The present invention also provides compositions comprising these recombinants for use in the pharmaceutical industry.

BACKGROUND OF THE INVENTION

The success of any pathogenic micro-organism lies in its ability to adapt to diversify, often under stressful conditions within the host. Pathogens have developed myriad ways of parallel metabolic pathways, complex regulatory systems and stress adaptive mechanisms which are best suited to the variety of environmental conditions they encounter within the human host. Organisms capable of utilizing N-acetylglucosamine (GlcNAc) as carbohydrate source are better adapted to infect and persist inside the host. The GlcNAc mutant of *Candida albicans* was avirulent in a murine model of systemic candidiasis (Singh, P., Ghosh, S., and Datta, A. (2001) Attenuation of virulence and changes in morphology in *Candida albicans* by disruption of the N-acetylglucosamine catabolic pathway. *Infect Immun* 69: 7898-7903). The dental plaque forming bacteria, *Streptococcus sobrinus* is more acidogenic than *Streptococcus mutans* but is less frequently isolated from human population as it is incapable of utilizing GlcNAc (Homer, K. A., Patel, R., and Beighton, D. (1993) Effects of N-acetylglucosamine on carbohydrate fermentation by *Streptococcus mutans* NCTC 10449 and *Streptococcus sobrinus* SL-1. *Infect Immun* 61: 295-302). The gram-negative opportunistic pathogen *Bacteroides fragilis* is reported to utilize N-acetyl-D-glucosamine more efficiently than glucose (Chen, H. C., Chang, C. C., Mau, W. J., and Yen L. S. (2002) Evaluation of N-acetylchitooligosaccharides as the main carbon sources for the growth of intestinal bacteria. *FEMS Microbiol Lett* 209: 53-56).

The gram-negative bacterium *Vibrio cholerae* is the causative agent of cholera, an acute dehydrating diarrhoeal disease, still endemic in many developing countries of the world. Pathogenesis of cholera involves ingestion of *V. cholerae* through contaminated food or water followed by its migration, after crossing the gastric acid barrier of the stomach, to the upper intestine where it has to penetrate the mucous layer for attachment to the intestinal epithelium. The bacterial growth within the host is largely dependent on the host derived macromolecules including mucin. The oligosaccharide side chains of these macromolecules are rich in amino sugars such as glucosamine and N-acetylglucosamine (GlcNAc), which can act as the source for nitrogen and carbon. Hence, it is not surprising that *V. cholerae* has an efficient system for the release, uptake and catabolism of these amino sugars.

Numerous enzymes are involved in the catabolization of the amino sugar, GlcNAc. In *E. coli* this amino sugar utilization and its regulation has been studied in detail where nagE-nagBACD are present as a divergent operon. NagC is a transcriptional regulator that represses this operon in the absence of environmental supply of amino sugars. GlcNAc catabolization converts glucosamine-6-phosphate to fructose-6-phosphate. In *V. cholerae*, enzymes involved in GlcNAc catabolization include β-N-acetylglucosaminidase, GlcNAc specific transporter, encoded by nagE, N-acetylglucosamine-6-phosphate deacetylase encoded by nagA1 and glucosamine-6-phosphate deaminase encoded by nagB. In *V. cholera*, nagA and nagC are co-transcribed and nagE is upstream of nagAC which is expressed in the opposite direction. In *V. cholerae*, nagE-nagAC exists as an operon but unlike *E. coli*, nagB is not present in the same operon. The region between nagE and nagB contains the cyclic AMP catabolic gene activator protein (CAP) binding site as well as NagC binding site (Plumbridge, J. (2001) DNA binding sites for Mlc and NagC proteins: regulation of nagE, encoding the N-acetylglucosamine transporter in *Escherichia coli*. Nucleic Acids Res 29: 506-514. Yamano, N., Oura, N., Wang, J., and Fujishima, S. (1997) Cloning and sequencing of the genes for N-acetylglucosamine use that construct divergent operons (nagE-nagAC) from *Vibrio cholerae* non-O1. *Biosci Biotechnol Biochem* 61: 1349-1353).

Presently, two variants of the oral vaccine for cholerae are in use, the WC-rBS and BivWC. WC-rBS, marketed as 'Dukoral', is a monovalent inactivated vaccine containing killed whole cells of *V. cholerae* O1 plus additional recombinant cholera toxin B subunit. BivWC, marketed as 'Shanchol' and 'mORCVAX', is a bivalent inactivated vaccine containing killed whole cells of *V. cholerae* O1 and *V. cholerae* O139. mORCVAX is available only in Vietnam. These oral vaccines provide protection in 52% of cases in the first year following vaccination and in 62% of cases in the second year.

There is a long felt need in the art for the inhibition and effective control of diseases caused by *Vibrio* spp., especially *V. cholerae*. Manipulation of pathogenic catabolic pathways vital for the sustenance of the pathogens in the host may prove to be an important method for the control and prevention of the pathogens.

U.S. Pat. No. 8,039,008 describes *Vibrio cholerae* comprising a mutated transcriptional regulatory protein (ToxT) amino acid sequence, wherein the mutation results in a reduction in the expression of cholera toxin by the *Vibrio cholerae*.

U.S. Pat. No. 6,203,799 describes *V. cholerae* vaccine strains which have a soft agar penetration-defective phenotype and lack a functional CtxA subunit. Further, methods for identifying new genes involved in *V. cholerae* motility and the cloning, identification, and sequencing of *V. cholerae* motB and fliC genes are disclosed.

US patent application 20120045475 describes a method for inhibiting or reducing colonization by a microbial pathogen in a subject or on a surface by administering to the subject or surface an effective amount of an agent that alters the expression of a polynucleotide selected from the group consisting of rbmA, rbmB, rbmC, rbmD, rbmE, rbmF and bapl or analogues or variants thereof.

Despite the availability of vaccines against cholera, there is a dire requirement for effective prevention and control of diseases caused by *V. cholerae*. In the present state of art, there is a lacuna in compositions that provide effective immunity against *V. cholerae* mediated diseases.

SUMMARY OF THE INVENTION

One aspect of the present invention relates to a recombinant strain of *Vibrio* species incapable of utilizing N-acetylglucosamine (GlcNAc), wherein the recombinant strain comprises at-least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species.

Another aspect of the present invention provides a composition comprising the recombinant strain of *Vibrio* species incapable of utilizing N-acetylglucosamine (GlcNAc), wherein the recombinant strain comprises at-least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species.

Yet another aspect of the present invention provides a vaccine comprising recombinant strain of *Vibrio* species incapable of utilizing N-acetylglucosamine (GlcNAc), wherein the recombinant strain comprises at least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species.

BRIEF DESCRIPTION OF THE DRAWINGS

FIG. 1A provides a hierarchical clustering of genes using an average linkage algorithm in *V. cholerae* El Tor strain CO-366 induced by Glucose or GlcNAc sugar. Vertical stripes represent genes, and columns show experimental samples at 60 mins after induction. $Log_2$-based color scale is presented at the bottom of the panels (red, induced; green, repressed). Black asterisks represent genes of the classical catabolic cascade while the grey ones show the genes acquired by certain members of Vibrionaceae family. The occurrence of a second cluster of genes (VC1781-N-acetylmannosamine-6-phosphate 2-epimerase; VC1782-N-acetylsamine kinase/ROK kinase and VC1783-nagA2) under the regulation of NagC is shown.

FIG. 1B provides the GlcNAc catabolic gene transcripts in *Vibrio cholerae* El Tor strain CO366 (wild type) in response to GlcNAc by quantitative RT-PCR assay. Error bars represent the coefficient of variation (n=3). RecA is the endogenous control.

FIG. 2A provides the organization of the genes involved in GlcNAc catabolism; hatched arrows represent the classical genes while open arrows represent the second cluster of the genes involved in GlcNAc catabolism.

FIG. 2B shows the growth pattern of *V. cholerae* El Tor strain CO366 (wild type) and GlcNAc-defective mutants on M9-Glucose (0.5%) and M9-GlcNAc (0.5%) plates. In the GlcNAc media, Sector 2 shows spotty growth of the mutant SHNE while sectors 3 and 4 show no growth of mutants SHNB and SHNA1-A2, respectively.

FIG. 3A shows the growth of *V. cholerae* El Tor strain CO366 (wild-type) and mutant strains in liquid M9-glucose. Error bars indicate co-efficient of variation.

FIG. 3B show the growth of *V. cholerae* El Tor strain CO366 (wild-type) and mutant strains in M9-GlcNAc media. SHNB and SHNA1-A2 mutants showed completely abolished growth and SHNE mutant showed reduced growth in GlcNAc media. Error bars indicate co-efficient of variation.

FIG. 3C shows the gene transcripts in *V. cholerae* El Tor strain CO366 (wild-type) and SHNE mutant strains in response to glucose or GlcNAc sugars. The names of the transcripts quantified by real-time-RT-PCR are indicated immediately below the bars.

FIG. 4A shows gene transcripts in *V. cholerae* El Tor strain CO366 (wild type), SHNA1, SHNA2 and SHNA1-A2 mutant strains in response to GlcNAc sugar. Error bars indicate co-efficient of variation (n=3). A coordinated expression of GlcNAc catabolic genes, nagA1 and nagA2 is observed.

FIG. 4B shows growth of SHNC mutant in liquid M9 media supplemented with non-fermentable carbon sources like glycerol and lactate. SHNC showed reduced growth on non-fermentable carbon sources like glycerol and lactate when compared with wild type.

FIG. 5A shows competition index (CI) of *V. cholerae* El Tor strain CO366 (~1), SHNA1-A2 (~0.0001), SHNE (~0.1) and SHNB (0.001) mutants strains. Six mice were taken per group. Each point is the CI data obtained from an individual mouse. The SHNA1-A2 and SHNB are significantly attenuated compared with the *V. cholerae* El Tor strain CO366 (wild-type) strain (P≤0.01 by Student's two-tailed t-test).

FIG. 5B shows the hierarchical clustering analysis of microarray expression data for genes found to be significantly regulated during growth of SHNC mutant in presence of glucose at 30 mins time point. Each of the genes is shown as vertical colored stripe. The most intense red and green colors correspond to increased or decreased expression values of 5 fold or more, respectively. Genes of the classical GlcNAc catabolic cluster (VC0994, VC0995) along with GlcNAc binding protein (VCA0811) and chemotactic protein (VC0449) are shown with black asterisks.

FIG. 6A shows virulence gene transcripts in *V. cholerae* El Tor strain CO366 (wild type), SHNA1-A2 and SHNE mutants in AKI medium, quantified by real-time-RT-PCR assay.

FIG. 6B shows hapR gene transcripts in *V. cholerae* El Tor strain CO366 (wild type), SHNA1, SHNA2, SHNA1-A2, SHNB and SHNE mutants in AKI medium, quantified by RT-PCR assay.

BRIEF DESCRIPTION OF THE SEQUENCES

SEQ ID NO: 1 shows the forward primer sequence that amplifies the upstream fragment of the putative translation site of nagA1 gene of *V. cholerae*

SEQ ID NO: 2 shows the reverse primer sequence that amplifies the upstream fragment of the putative translation site of nagA1 gene of *V. cholerae*

SEQ ID NO: 3 shows the forward primer sequence that amplifies the downstream fragment of the putative translation site of nagA1 gene of *V. cholerae*

SEQ ID NO: 4 shows the reverse primer sequence that amplifies the downstream fragment of the putative translation site of nagA1 gene of *V. cholerae*

SEQ ID NO: 5 shows the forward primer sequence that amplifies the upstream fragment of the putative translation site of nagB gene of V. cholerae

SEQ ID NO: 6 shows the reverse primer sequence that amplifies the upstream fragment of the putative translation site of nagB gene of *V. cholerae*

SEQ ID NO: 7 shows the forward primer sequence that amplifies the downstream fragment of the putative translation site of nagB gene of *V. cholerae*

SEQ ID NO: 8 shows the reverse primer sequence that amplifies the downstream fragment of the putative translation site of nagB gene of *V. cholerae*

SEQ ID NO: 9 shows the forward primer sequence that amplifies the upstream fragment of the putative translation site of nagA2 gene of *V. cholerae*

SEQ ID NO: 10 shows the reverse primer sequence that amplifies the upstream fragment of the putative translation site of nagA2 gene of *V. cholerae*

SEQ ID NO: 11 shows the forward primer sequence that amplifies the downstream fragment of the putative translation site of nagA2 gene of *V. cholerae*

SEQ ID NO: 12 shows the reverse primer sequence that amplifies the downstream fragment of the putative translation site of nagA2 gene of *V. cholerae*

SEQ ID NO: 13 shows the forward primer sequence that amplifies the upstream fragment of the putative translation site of nagC gene of *V. cholerae*

SEQ ID NO: 14 shows the reverse primer sequence that amplifies the upstream fragment of the putative translation site of nagC gene of *V. cholerae*

SEQ ID NO: 15 shows the forward primer sequence that amplifies the downstream fragment of the putative translation site of nagC gene of *V. cholerae*

SEQ ID NO: 16 shows the reverse primer sequence that amplifies the downstream fragment of the putative translation site of nagC gene of *V. cholerae*

SEQ ID NO: 17 shows the forward primer sequence that amplifies the upstream fragment of the putative translation site of nagE gene of *V. cholerae*

SEQ ID NO: 18 shows the reverse primer sequence that amplifies the upstream fragment of the putative translation site of nagE gene of *V. cholerae*

SEQ ID NO: 19 shows the forward primer sequence that amplifies the downstream fragment of the putative translation site of nagE gene of *V. cholerae*

SEQ ID NO: 20 shows the reverse primer sequence that amplifies the downstream fragment of the putative translation site of nagE gene of *V. cholerae*

SEQ ID NO: 21 shows the forward primer sequence that amplifies the upstream fragment of the putative translation site of vc1781 gene of *V. cholerae*

SEQ ID NO: 22 shows the reverse primer sequence that amplifies the upstream fragment of the putative translation site of vc1781 gene of *V. cholerae*

SEQ ID NO: 23 shows the forward primer sequence that amplifies the downstream fragment of the putative translation site of vc1781 gene of *V. cholerae*

SEQ ID NO: 24 shows the reverse primer sequence that amplifies the downstream fragment of the putative translation site of vc1781 gene of *V. cholerae*

SEQ ID NO: 25 shows the forward primer sequence that amplifies the upstream fragment of the putative translation site of vc1782 gene of *V. cholerae*

SEQ ID NO: 26 shows the reverse primer sequence that amplifies the upstream fragment of the putative translation site of vc1782 gene of *V. cholerae*

SEQ ID NO: 27 shows the forward primer sequence that amplifies the downstream fragment of the putative translation site of vc1782 gene of *V. cholerae*

SEQ ID NO: 28 shows the reverse primer sequence that amplifies the downstream fragment of the putative translation site of vc1782 gene of *V. cholerae*

DETAILED DESCRIPTION OF THE INVENTION

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

In accordance with the present invention, there may be employed conventional molecular biology, microbiology, and recombinant DNA techniques within the skill of the art. Such techniques are fully explained in the literature.

Definitions

For convenience, before further description of the present invention, certain terms employed in the specification, examples and appended claims are provided here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a," "an" and "the" are used to refer to one or to more than one (i.e., to at least one) of the grammatical object of the article.

Throughout this specification, unless the context requires otherwise the word "comprise", and variations such as "comprises" and "comprising", will be understood to imply the inclusion of a stated element or step or group of element or steps but not the exclusion of any other element or step or group of element or steps. It is not intended to be construed as "consists of only."

The term "primer" as used herein refers to a single-stranded oligonucleotide, the 3' end of which can be used as the initiation site for the DNA synthesis with a DNA polymerase. As used herein, the term "primer sequence" refers to the sequence of the primer or the complementary sequence.

The term "recombinant" means a cell or organism in which genetic recombination has occurred. It also includes a molecule (e.g., a nucleic acid or a polypeptide) that has been artificially or synthetically (i.e., non-naturally) altered by human intervention. The alteration can be performed on the molecule within, or removed from, its natural environment or state.

The term "mutant" and "mutation" may mean any detectable change in genetic material, e.g., DNA or any process, mechanism or result of such a change. This includes gene mutations, in which the structure (e.g., DNA sequence) of a gene is altered, any gene or DNA arising from any mutation process and any expression product (e.g., RNA, protein or enzyme) expressed by a modified gene or DNA sequence.

The term "variant" may be use to indicate a modified or altered gene, DNA sequence, RNA, enzyme, cell etc, ie, any kind of mutant.

The terms "recombinant" and "mutant" are herein used interchangeably.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence.

The terms "vector", "cloning vector" and "expression vector" mean the vehicle by which a DNA or RNA sequence (e.g., a foreign gene) can be introduced into a host cell so as to transform the host and promote expression (e.g., transcription and translation) of the introduced sequence. Vectors may include plasmids, phages, viruses, etc.

The present invention features mutants of *Vibrio cholerae* unable to utilize the amino sugar, N-acetylgucosamine (GlcNAc) and possess an impaired ability to colonize.

The present invention provides recombinant strains of *Vibrio cholerae* that are produced by recombinant DNA technology. The present invention provides recombinant strains or mutants of *Vibrio cholerae* with at least one mutated gene involved in the GlcNAc catabolic pathway. The present invention provides a composition comprising recombinant strains of *V. cholerae* with impaired GlcNAc utilization and reduced colonization in the host. Compositions comprising the mutant strains of *V. cholerae* of the present invention can be used in myriad ways including vaccines for inducing immunity in hosts against the *V. cholerae* pathogens and for effective prevention against *V. cholerae* mediated diseases.

The recombinant strains of *Vibrio cholerae* of the present invention are created by disruptions in one or more of following genes: nagA1 (N-acetylglucosamine-6-phosphate deacetylase/deacetylase I; mutant SHNA1), nagA2 (N-acetylglucosamine-6-phosphate deacetylase II/vc1783; mutant SHNA2), nagB (glucosamine-6-phosphate deaminase/isomerase; mutant SHNB), nagC (N-acetylglucosamine specific repressor; mutant SHNC), nagE (GlcNAc transporter/PTS-transporter; mutant SHNE), vc1781 (N-acetylmannosamine-6-phosphate 2-epimerase; mutant SHVC1781) and vc1782 (N-acetylmannosamine kinase/ROK kinase; mutant SHVC1782).

The inventors of the present invention found unexpected and surprising results when microarray analysis of wild type *Vibrio cholerae* El Tor strain CO366 grown either in the presence of glucose or GlcNAc sugars revealed an up-regulation of GlcNAc catabolic genes (FIGS. 1A and 1B). Further analysis revealed that the GlcNAc catabolic genes are present in two distinct clusters (FIG. 2A), where the second cluster of genes encompassing N-acetylmannosamine-6-phosphate 2-epimerase (cmr.jcvi.orgVC1781), N-acetylmannosamine kinase/ROK kinase (cmr.jcvi.org: VC1782) and N-acetylglucosamine 6-phosphate deacetylase 2 (nagA2; cmr.jcvi.org: VC1783) fall within the VPI-2 cluster known to be involved in sialic acid metabolism. The nagA2 appears to be a homolog of the classical GlcNAc catabolic gene, nagA1.

In *Vibrio cholerae*, the GlcNAc catabolic pathway is highly specialized for the successful establishment of the pathogen in its preferred colonization site, during the critical early phase of infection. The bacterium uses the GlcNAc monosaccharide as a nutrient source to reach sufficient titers in the gut. A disruption in the GlcNAc catabolic cascade affects the capacity of *V. cholerae* to utilize the amino-sugar in the intestinal environment, as a result of which the organism loses its overall fitness to establish itself in a nutrient limited condition. The occurrence of more than one cluster of GlcNAc catabolic genes with similar functions within the genome of *Vibrio cholerae*, suggest an efficient catabolism of GlcNAc saccharide. *V. cholerae*, by acquiring two copies of deacetylase (nagA1 and nagA2), GlcNAc kinase (PTS transporter/VC0995) and ROK kinase), and simultaneously achieving a co-ordinated expression of the two copies of deacetylase genes nagA1 and nagA2, is highly adapted for colonization in the host as a pathogen. Thus, producing mutants of *V. cholerae* which show impaired colonization in the host and impaired GlcNAc utilization thereby leading to reduced or compromised virulence is advantageous for the prevention and control of diseases caused by *V. cholerae*.

Without wishing to bind to a specific theory, the inventors believe that the N-acetylglucosamine specific repressor, NagC, performs a dual role. The classical GlcNAc catabolic genes are under its negative control while the genes belonging to the second cluster are positively regulated by it. In *V. cholerae*, NagC exerts a global regulation that allows cells to selectively assimilate a preferred compound among a mixture of several potential carbon sources (FIG. 2A).

The recombinant strains of *Vibrio cholerae* as disclosed in the present invention, unable to utilize GlcNAc were created by at least one mutation in at least one of the genes, both classical and the second cluster, involved in the GlcNAc catabolic pathway, wherein the recombinant *V. cholerae* strain having mutation in the nagA1 is designated as SHNA1, the recombinant *V. cholerae* strain having mutation in the nagA2 is designated as SHNA2, the recombinant *V. cholerae* strain having mutation in the nagB is designated as SHNB, the recombinant *V. cholerae* strain having mutation in the nagC is designated as SHNC, the recombinant *V. cholerae* strain having mutation in the nagE is designated as SHNE, the recombinant *V. cholerae* strain having mutation in the vc1781 is designated as SHVC1781 and the recombinant *V. cholerae* strain having mutation in the vc1782 gene is designated as SHVC1782.

The recombinant strains may be produced by site-directed mutagenesis in the desired genes. The mutations may be addition, substitution or deletion in the region of translational site of the desired genes of *Vibrio* species.

The recombinant strains were created by non-polar deletions in the gene of interest in the wild type strain *V. cholerae* El Tor strain CO366 (Example 2). In-frame deletions were carried out by the use of cross-over polymerase chain reaction (PCR) assays. The recombinant *V. cholerae* strain comprising mutations in more than one gene was also created. A recombinant *V. cholerae* strain comprising double mutation, i.e., mutation in the nagA1 and nagA2 genes was created and designated as SHNA1-A2 (Example 3).

Differential growth response was observed for the recombinant *V. cholerae* strains in glucose and GlcNAc supplemented media. All the recombinant *V. cholerae* strains were able to grow on M9-glucose supplemented media but, on M9-GlcNAc supplemented media, the strains showed retarded growth or failed to grow at all (FIG. 2B). Amongst the recombinant strains, SHNE showed reduced growth, SHNA1-A2 and SHNB showed complete arrest of growth in M9-GlcNAc supplemented media (FIGS. 3A, 3B and 3C).

Microarray analysis of the wild type *Vibrio cholerae* and SHNC mutant strains grown in the presence of glucose showed that nagA1, nagE, and nagB genes were upregulated in the SHNC recombinant. SHNC recombinant strains grown in the presence of GlcNAc showed a down regulation of nagA2 and ROK kinase genes (VC1776-VC1784; Table 4).

The recombinant strains of *V. cholerae*, SHNA1-A2, comprising mutations in the nagA1 and nagA2 genes shows complete inhibition of growth on GlcNAc media whereas a single mutant, SHNA1 or SHNA2 is able to grow on GlcNAc media. However, there is a difference in the growth rate of the mutants when compared to wild type, *V. cholerae* El Tor strain CO366 (FIGS. 3A and 3B). The transcript levels of nagA2 is up-regulated by almost 13-fold in SHNA1 mutant in the presence of GlcNAc sugar compared to ~6-fold up-regulation in the wild type strain suggesting a coordinated regulation of both the copies of deacetylase genes in *V. cholerae* (FIG. 4A). NagC mutants also showed decreased growth in liquid M9 media supplemented with non-fermentable carbon sources like glycerol and lactate (FIG. 4B). Similar compromised growth was also seen on M9-glycerol agar plate study.

The recombinant strains of *V. cholerae* as disclosed in the present invention were unable to survive and multiply in the host cell because of the lost capacity to utilize the host derived macromolecules like GlcNAc sugars, lead to the impaired colonization of the strains in the host. The property of impaired colonization thereby leads to a decrease in the persistence of infection, making them ideal candidates for vaccine strains. The recombinant strains of *V. cholerae*, SHNE, SHNB and SHNA1-SHNA2, showed reduced intestinal colonization in in-vivo studies. The analysis with respect to the wild type *V. cholerae* revealed that the colonization efficiency of the recombinant SHNA1-A2 was nil; that of the recombinant SHNE strains was reduced by more than 10 folds and that of the SHNB recombinant strains was attenuated by more than 1000 folds (FIG. 5A).

The recombinant *V. cholerae* strains with reduced colonization abilities and an inability to utilize GlcNAc have surprisingly no significant changes in their virulence or toxin gene transcript levels indicating them as ideal candidates for vaccines (FIGS. 6A and 6B). Nonetheless, these strains can be highly antigenic and have strong immunogenicity. When combined with mutations in the GlcNAc catabolic genes nagE, nagB and two copies of nagA genes, the GlcNAc-defective mutations result in strains which are excellent candidates for vaccines for the prevention of cholerae in humans. However, these recombinant strains display increased constitutive expression of toxin, Tcp pili and hapR genes (FIGS. 6A and 6B). This increased expression may account for the enhanced immunogenicity of these strains.

One embodiment of the present invention provides a recombinant strain of *Vibrio* species incapable of utilizing N-acetylglucosamine (GlcNAc), wherein the recombinant strain comprises at-least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species.

In another embodiment of the present invention, there is provided a recombinant strain of *Vibrio* species incapable of utilizing N-acetylglucosamine (GlcNAc), wherein the recombinant strain comprises at-least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species, wherein the mutation is selected from a group consisting of deletion, addition, and substitution.

In another embodiment of the present invention, there is provided a recombinant strain of *Vibrio* species incapable of utilizing N-acetylglucosamine (GlcNAc), wherein the recombinant strain comprises at-least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species, wherein the mutation is selected from a group consisting of deletion, addition, and substitution, is a non-polar deletion.

In a further embodiment of the present invention, there is provided a recombinant strain of *Vibrio* species incapable of utilizing N-acetylglucosamine (GlcNAc), wherein the recombinant strain comprises at-least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species, wherein the host is a human or animal.

In yet another embodiment of the present invention, there is provided a recombinant strain of *Vibrio* species incapable of utilizing N-acetylglucosamine (GlcNAc), wherein the recombinant strain comprises at-least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species, wherein the *Vibrio* species is *Vibrio cholera*.

In yet another embodiment of the present invention, there is provided a recombinant strain of *Vibrio* species incapable of utilizing N-acetylglucosamine (GlcNAc), wherein the recombinant strain comprises at-least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species, wherein the *Vibrio* species is *Vibrio cholera* El Tor strain CO366.

Another embodiment of the present invention provides a composition comprising the recombinant strain of *Vibrio* species incapable of utilizing N-acetylglucosamine (GlcNAc), wherein the recombinant strain comprises at-least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species.

Another embodiment of the present invention provides a vaccine comprising the recombinant strain of *Vibrio* species incapable of utilizing N-acetylglucosamine (GlcNAc), wherein the recombinant strain comprises at-least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species.

In another embodiment of the present invention there is provided a composition comprising the recombinant strain of *Vibrio* species incapable of utilizing N-acetylglucosamine (GlcNAc), wherein the recombinant strain comprises at-least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species, wherein the composition optionally comprises a pharmaceutically acceptable carrier, diluent, adjuvant, and/or additive.

In yet another embodiment of the present invention there is provided a vaccine comprising the recombinant strain of *Vibrio* species incapable of utilizing N-acetylglucosamine (GlcNAc), wherein the recombinant strain comprises at-least one mutation in at-least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein the recombinant strain shows impaired colonization in a host as compared to a wild type *Vibrio* species, wherein the vaccine optionally comprises a pharmaceutically acceptable carrier, diluent, adjuvant, and/or additive.

The mutants of the cholera causing bacterium, *Vibrio cholerae*, of the present invention show defective GlcNAc utilization abilities and drastic reduction in colonization of the host intestine. Although the GlcNAc catabolism and colonization of these mutants are impaired, there is no related decrease in virulence gene transcript levels indicating that these mutant strains can be ideal vaccine strains for the effective prevention of cholera.

The present invention is not to be limited in scope by the specific embodiments described herein, which are intended for the purposes of exemplification only. Functionally-equivalent products, compositions, and methods are clearly within the scope of the invention, as described herein.

EXAMPLES

The disclosure will now be illustrated with working examples, which is intended to illustrate the working of disclosure and not intended to take restrictively to imply any limitations on the scope of the present disclosure.

Example 1

Bacterial Strains, Plasmids and Culture Conditions

*V. cholerae* El Tor strain CO366 was used as the wild type strain.

*E. coli* (DH5α) and *V. cholerae* strains were propagated at 37° C. in Luria Broth (LB) medium, containing ampicillin 75 μg/ml, polymixin B 20 Units/ml and streptomycin 30 μg/ml at 37° C. The suicide vector, pCVD442 was used for the molecular biology studies. pCVD442 is a suicide plasmid used for gene allele exchange in bacteria and is composed of the mob, ori, and bla regions in addition to the sacB gene and ampicillin resistant marker gene. sacB gene provides a conditionally lethal phenotype. The sacB locus encodes the enzyme levan sucrase, which is toxic for gram-negative organisms only in the presence of sucrose.

Luria Broth (LB) Medium

The LB medium was prepared using 1% tryptone, 1% NaCl and 0-5% yeast extract (pH 8.0).

M9 Medium $Na_2HPO_4$ 6 g, $KH_2PO_4$ 3 g, NaCl 0.5 g, $NH_4Cl$ 1 g and Casamino acid 2 g were added per litre of distilled water. The pH of the media was adjusted to 7.4, autoclaved and cooled. 1M $MgCl_2$ 2 ml, 0.1 ml of 1M $CaCl_2$ and 10 ml of filter-sterilized 20% Glucose or GlcNAc were added to the media. For plate studies, 1.5% agar was also added to the media.

AKI Media

AKI medium was prepared using 1.5% Bacto peptone, 0.4% yeast extract, 0.5% NaCl and 0.3% $NaHCO_3$. Studies on inducing virulence genes were carried out in AKI medium at 30° C.

Example 2

Preparation of SHNA1 (nagA1—N-acetylglucosamine deacetylase/deacetylase I)

Construction of Plasmid Vector pCVD442-ΔNA1

A PCR assay with primers NA1UF (SEQ ID NO: 1) and NA1UR (SEQ ID NO: 2) were used for amplification of the region 503 bp upstream of the putative translational start site of nagA1 to obtain an amplified product of 503 bp. Primers NA1DF (SEQ ID NO: 3) and NA1DR (SEQ ID NO: 4) were used for the amplification of the region 588 bp downstream of nagA1 to obtain an amplified product of 588 bp.

For each set of PCR analysis, the reaction volume comprised the specific primers, genomic DNA, 10×PCR buffer with $Mgcl_2$, dNTPs mix and Taq DNA polymerase. The reaction volume was 25 μl. PCR parameters for amplifying upstream and downstream fragment are provided in Table 2.

The PCR products of 503 bp and 588 bp, resulting from AmpliTaq polymerase PCR with primer sets NA1UF and NA1UR, and NA1DF and NA1DR, were purified by two passages over the QiaQuick PCR purification kit (Qiagen Inc).

Cross Over PCR

The primers NA1UR and NA1DF have 23 bp of overlapping nucleotide sequence, such that the crossover PCR brings the downstream region of NAGA1 after stop codon to the upstream region before the start codon of NAGA1. The upstream and downstream fragments were mixed in equimolar ratio and used for cross-over PCR with primers NA1UF and NA1DR to delete the ORF. For the cross-over PCR analysis, the reaction volume of 25 μl comprised the crossover primers, 10×PCR buffer with $Mgcl_2$, dNTPs mix and Taq DNA polymerase. The PCR parameters for the cross-over PCR assay is provided in Table 3.

The cross-over PCR product of 1091 bp was purified by two passages over the QiaQuick PCR purification kit (Qiagen Inc). The amplified and purified product of crossover PCR assay was then ligated using NEB T4DNA-ligase to the counter-selectable plasmid pCVD442 digested with EcoRV to generate plasmid pCVD442-ΔNA1. The plasmid is counter selected using ampicillin and sucrose.

Non-Polar Deletion for Generation of Mutant nagA1

The plasmid pCVD442-ΔNA1 was introduced into *V. cholerae* O1 El Tor strain, CO 366 by bi-parental mating or conjugation on an LB agar plate. Four co-integrants, formed after conjugation of CO-366 and *E. coli* harbouring the plasmid pCVD442-ΔNA1, were purified by streaking, once under selection and then passaged once without selection, to allow recombination to occur. Sixteen independent colonies were then streaked on the counter-selection medium (LB medium containing ampicillin and polymixin B). The ampicillin and polymixin B resistant colonies were next streaked on LB medium without NaCl but containing 6% sucrose for sucrose-based selection. Best results were achieved when counter selection plates were incubated at room temperature for 2 days.

The non-polar deletion mutants of nagA1 were confirmed by PCR assay. The strains were checked using the primers NA1UF and NA1DR. The sizes of the amplified products were 2.228 kb in wild type strain and 1.091 kb in the mutants. The size of the ORF deleted in the mutants was 1137 bp. The non-polar deletion mutants of nagA1 were denoted as SHNA1.

Preparation of SHNB (nagB—N-acetylglucosamine Deaminase)

Construction of Plasmid Vector pCVD442-ΔNB

A PCR assay with primers NBUF (SEQ ID NO: 5) and NBUR (SEQ ID NO: 6) were used for amplification of the region 510 bp upstream of the putative translational start site of nagB to obtain an amplified product of 510 bp. Primers NBDF (SEQ ID NO: 7) and NBDR (SEQ ID NO: 8) were used for the amplification of the region 519 bp downstream of nagA1 to obtain an amplified product of 519 bp.

For each set of PCR analysis, the reaction volume comprised the specific primers, genomic DNA, 10×PCR buffer with Mgcl$_2$, dNTPs mix and Taq DNA polymerase. The reaction volume was 25 µl. PCR parameters for amplifying upstream and downstream fragment are provided in Table 2.

The PCR products of 510 bp and 519 bp, resulting from AmpliTaq polymerase PCR with primer sets, NBUF and NBUR, and NBDF and NBDR, were purified by two passages over the QiaQuick PCR purification kit.

Cross Over PCR

The primers NBUR and NBDF have 23 bp of overlapping nucleotide sequence, such that the crossover PCR brings the downstream region of nagB after stop codon to the upstream region before the start codon of nagB. The upstream and downstream fragments were mixed in equimolar ratio and used for cross-over PCR with primers NBUF (SEQ ID NO: 5) and NBDR (SEQ ID NO: 8) to delete the ORF. For the cross-over PCR analysis, the reaction volume of 25 µl comprised the crossover primers, 10×PCR buffer with Mgcl$_2$, dNTPs mix and Taq DNA polymerase. The PCR parameters for the cross-over PCR assay is provided in Table 3.

The cross-over PCR product of size 1029 bp was purified by two passages over the QiaQuick PCR purification kit. The crossover fragment was then ligated using NEB T4DNA-ligase to the ampicillin and sucrose based counter-selectable plasmid pCVD442 digested with EcoRV to generate plasmid pCVD442-ΔNB.

Non-Polar Deletion for Generation of Mutant nagB

The plasmid pCVD442-ΔNB was introduced into *V. cholerae* O1 El Tor strain, CO 366 by bi-parental mating or conjugation on an LB agar plate.

Four co-integrants, formed after conjugation of *V. cholerae* O1 El Tor CO-366 and *E. coli* harbouring the plasmid pCVD442-ΔNB, were purified by streaking once under selection and then were passaged once without selection to allow recombination to occur. Sixteen independent colonies were then streaked on the counter-selection medium—the LB medium containing ampicillin and polymixin B. The ampicillin and polymixin B resistant colonies were next streaked on LB medium without NaCl but containing 6% sucrose for sucrose-based selection. Best results were achieved when counter-selection plates were incubated at room temperature for 2 days.

The non-polar deletion mutants of nagB were confirmed by PCR assay. The strains were checked using the primers NBUF and NBDR. The sizes of the amplified products were 2.830 kb in wild type strain and 1.029 kb in the mutants. The size of the ORF deleted in the mutants was 801 bp. The non-polar deletion mutants of nagB were denoted as SHNB.

Preparation of SHNA2 (nagA2; deacetylase II/VC1783)

Construction of Plasmid Vector pCVD442-ΔNA2

A PCR assay with primers NA2UF (SEQ ID NO: 9) and NA2UR (SEQ ID NO: 10) were used for amplification of the region 459 bp upstream of the putative translational start site of nagA2 to obtain an amplified product of 459 bp. The primers NA2DF (SEQ ID NO: 11) and NA2DR (SEQ ID NO: 12) were used for the amplification of the region 486 bp downstream of nagA2 to obtain an amplified product of 486 bp.

For each set of PCR analysis, the reaction volume comprised the specific primers, genomic DNA, 10×PCR buffer with Mgcl$_2$, dNTPs mix and Taq DNA polymerase. The reaction volume was 25 µl. PCR parameters for amplifying upstream and downstream fragment are provided in Table 2.

The PCR products of 459 bp resulting from AmpliTaq polymerase PCR with primer sets NA2UF and NA2UR and product of 486 bp resulting from a PCR assay with the NA2DF and NA2DR primer sets were purified by two passages over the QiaQuick PCR purification kit (Qiagen).

Cross Over PCR

The primers NA2UR (SEQ ID NO: 10) and NA2DF (SEQ ID NO: 11) have 23 bp of overlapping nucleotide sequence, such that the crossover PCR brings the downstream region of nagA2 after stop codon to the upstream region before the start codon of nagA2. The amplified products (upstream and downstream fragments) were mixed in equimolar ratio and used for cross-over PCR with primers NA2UF and NA2DR to delete the ORF. For the cross-over PCR analysis, the reaction volume of 25 µl comprised the crossover primers, 10×PCR buffer with Mgcl$_2$, dNTPs mix and Taq DNA polymerase. The PCR parameters for the cross-over PCR assay is provided in Table 3.

The PCR product size was 945 bp. The cross-over PCR product of 945 bp was purified by two passages over the QiaQuick PCR purification kit (Qiagen). The crossover fragment was then ligated using NEB T4DNA-ligase to the ampicillin and sucrose based counter-selectable plasmid, pCVD442 digested with EcoRV to generate the recombinant vector plasmid, pCVD442-ΔNA2.

Non-Polar Deletion for Generation of Mutant nagA2

The plasmid pCVD442-ΔNA2 was introduced into *V. cholerae* O1 El Tor strain, CO 366 by bi-parental mating or conjugation on an LB agar plate.

Four co-integrants, formed after conjugation of CO-366 and *E. coli* harbouring the plasmid pCVD442-ΔNA2, were purified by streaking one time under selection and then were passaged one time without selection to allow recombination to occur. Sixteen independent colonies were then streaked on the counter-selection medium—the LB medium containing ampicillin and polymixin B. The ampicillin and polymixin B resistant colonies were next streaked on LB medium without NaCl but containing 6% sucrose for sucrose-based selection. Best results were achieved when counter-selection plates were incubated at room temperature for 2 days.

The non-polar deletion mutants of nagA2 were confirmed by PCR assay. The strains were checked using the primers NA2UF and NA2DR. The sizes of the amplified products were 2.082 kb in wild type strain and 945 kb in the mutants.

The size of the ORF deleted in the mutants was 1137 bp. The non-polar deletion mutants of nagA2 were denoted as SHNA2.

Preparation of SHNC (nagC; N-acetylglucosamine Specific Repressor)

Construction of Plasmid Vector pCVD442-ΔNC

A PCR assay with primers NCUF (SEQ ID NO: 13) and NCUR (SEQ ID NO: 14) were used for the amplification of the region 616 bp upstream of the putative translational start site of nagC to obtain an amplified product of 616 bp. The primers NCDF (SEQ ID NO: 15) and NCDR (SEQ ID NO: 16) were used for the amplification of the region 432 bp downstream of nagC to obtain an amplified product of 432 bp.

For each set of PCR analysis, the reaction volume comprised the specific primers, genomic DNA, 10×PCR buffer with $Mgcl_2$, dNTPs mix and Taq DNA polymerase. The reaction volume was 25 µl. PCR parameters for amplifying upstream and downstream fragment are provided in Table 2.

The PCR products of 616 bp and 432 bp resulting from AmpliTaq polymerase PCR with primer sets NCUF and NCUR and NCDF and NCDR, respectively, were purified by two passages over the QiaQuick PCR purification kit (Qiagen).

Cross Over PCR

The primers NCUR (SEQ ID NO: 14) and NCDF (SEQ ID NO: 15) have 23 bp of overlapping nucleotide sequence, such that the crossover PCR brings the downstream region of nagC after stop codon to the upstream region before the start codon of nagC. The amplified products or the upstream and downstream fragments were mixed in equimolar ratio and used for cross-over PCR with primers NCUF and NCDR to delete the ORF. For the cross-over PCR analysis, the reaction volume of 25 µl comprised the crossover primers, 10×PCR buffer with $Mgcl_2$, dNTPs mix and Taq DNA polymerase. The PCR parameters for the cross-over PCR assay is provided in Table 3.

The crossover PCR assay yielded an amplified product of size 1048 bp which was purified using the QiaQuick PCR purification kit (Qiagen). The amplified product obtained from the croosover PCR assay was then ligated using NEB T4DNA-ligase into the ampicillin and sucrose based counter-selectable plasmid pCVD442, digested with EcoRV to generate the recombinant plasmid, pCVD442-ΔNC.

Non-Polar Deletion for Generation of Mutant nagC

The plasmid pCVD442-ΔNC was introduced into *V. cholerae* El Tor strain, CO 366 by bi-parental mating or conjugation on an LB agar plate.

Four co-integrants, formed after conjugation of *V. cholerae* El Tor strain CO-366 and *E. coli* harbouring the plasmid pCVD442-ΔNC, were purified by streaking one time under selection and then were passaged one time without selection to allow recombination to occur. Sixteen independent colonies were then streaked on the counter-selection medium—the LB medium containing ampicillin and polymixin B. The ampicillin and polymixin B resistant colonies were next streaked on LB medium without NaCl but containing 6% sucrose for sucrose-based selection. Best results were achieved when counter-selection plates were incubated at room temperature for 2 days.

The non-polar deletion mutants of nagC were confirmed by PCR assay. The strains were checked using the primers NCUF and NCDR. The sizes of the amplified products were 2.263 kb in wild type strain and 1.048 kb in the mutants. The size of the ORF deleted in the mutants was 1215 bp. The non-polar deletion mutants of nagC were denoted as SHNC.

Preparation of SHNE (nagE; GlcNAc Transporter, PTS-Transporter)

Construction of Plasmid Vector pCVD442-ΔNE

A PCR assay with primers NEUF (SEQ ID NO: 17) and NEUR (SEQ ID NO: 18) were used for the amplification of the region 505 bp upstream of the putative translational start site of nagE to obtain an amplified product of 505 bp. Primers NEDF (SEQ ID NO: 19) and NEDR (SEQ ID NO: 20) were used for the amplification of the region 577 bp downstream of nagE to obtain an amplified product of 577 bp.

A PCR assay with AmpliTaq polymerase and the primer set NEUF (SEQ ID NO: 17) and NEUR (SEQ ID NO: 18) resulted in an amplified product of size 505 bp (upstream fragment). Another PCR assay with AmpliTaq polymerase and the primer set NEDF (SEQ ID NO: 19) and NEDR (SEQ ID NO: 20) resulted in an amplified product of size 577 bp (downstream fragment). For each set of PCR analysis, the reaction volume comprised the specific primers, genomic DNA, 10×PCR buffer with $Mgcl_2$, dNTPs mix and Taq DNA polymerase. The reaction volume was 25 µl. PCR parameters for amplifying upstream and downstream fragment are provided in Table 2. The amplified products were further purified by two passages over the QiaQuick PCR purification kit (Qiagen).

Crossover PCR Assay

The primers NEUR (SEQ ID NO: 18) and NEDF (SEQ ID NO: 19) have 23 bp of overlapping nucleotide sequence, such that the crossover PCR brings the downstream region of nagE after stop codon to the upstream region before the start codon of nagE. The amplified products (upstream and downstream fragments) were mixed in equimolar ratio and used for a cross-over PCR assay with the primers NEUF and NEDR to delete the ORF. For the cross-over PCR analysis, the reaction volume of 25 µl comprised the crossover primers, 10×PCR buffer with $Mgcl_2$, dNTPs mix and Taq DNA polymerase. The PCR parameters for the cross-over PCR assay is provided in Table 3.

An amplified product of size 1082 bp was obtained and purified by two passages over the QiaQuick PCR purification kit (Qiagen). The amplified product obtained by the crossover PCR assay was then ligated using NEB T4DNA-ligase into the ampicillin and sucrose based counter-selectable plasmid pCVD442, digested with EcoRV to generate the recombinant plasmid, pCVD442-ΔNE.

Non-Polar Deletion for Generation of Mutant nagE

The plasmid pCVD442-ΔNE was introduced into *V. cholerae* O1 El Tor strain, CO 366 by bi-parental mating or conjugation on an LB agar plate.

Four co-integrants, formed after conjugation of *V. cholerae* O1 El Tor strain CO-366 and *E. coli* harbouring the plasmid pCVD442-ΔNE, were purified by streaking one time under selection and then were passaged one time without selection to allow recombination to occur. Sixteen independent colonies were then streaked on the counter-selection medium—the LB medium containing ampicillin and polymixin B. The ampicillin and polymixin B resistant colonies were next streaked on LB medium without NaCl but containing 6% sucrose for sucrose-based selection.

The non-polar deletion mutants of nagE were confirmed by PCR assay. The strains were checked using the primers NEUF and NEDR. The sizes of the amplified products were 2.653 kb in the wild type strain and 1.082 kb in the mutant strain. The size of the ORF deleted in the mutants was 1572 bp. The non-polar deletion mutants of nagE were denoted as SHNE.

Preparation of SHVC1781
(N-acetylmannosamine-6-phosphate 2-epimerase; vc1781)

Construction of Plasmid Vector pCVD442-Δ1781

A PCR assay with primers 1781UF (SEQ ID NO: 21) and 1781UR (SEQ ID NO: 22) were used for amplification of the region 474 bp upstream of the putative translational start site of vc1781 to obtain an amplified product of 474 bp. The primers 1781DF (SEQ ID NO: 23) and 1781DR (SEQ ID NO: 24) were used for the amplification of the region 475 bp downstream of vc1781 to obtain an amplified product of 475 bp.

For each set of PCR analysis, the reaction volume comprised the specific primers, genomic DNA, 10×PCR buffer with $Mgcl_2$, dNTPs mix and Taq DNA polymerase. The reaction volume was 25 μl. PCR parameters for amplifying upstream and downstream fragment are provided in Table 2.

The amplified products (upstream and downstream fragments) were purified by two passages over the QiaQuick PCR purification kit (Qiagen).

Cross-Over PCR Assay

The primers 1781UR (SEQ ID NO: 22) and 1781DF (SEQ ID NO: 23) have 23 bp of overlapping nucleotide sequence, such that the crossover PCR brings the downstream region of vc1781 after stop codon to the upstream region before the start codon of vc1781. The upstream and downstream fragments were mixed in equimolar ratio and used for cross-over PCR with primers 1781UR (SEQ ID NO: 22) and 1781DF (SEQ ID NO: 23) to delete the ORF. For the cross-over PCR analysis, the reaction volume of 25 μl comprised the cross-over primers, 10×PCR buffer with $Mgcl_2$, dNTPs mix and Taq DNA polymerase. The PCR parameters for the cross-over PCR assay is provided in Table 3.

The cross-over PCR assay resulted in an amplified product of size 949 bp. The amplified product was purified by two passages over the QiaQuick PCR purification kit (Qiagen). The amplified and purified product of the cross-over PCR assay was then ligated using NEB T4DNA-ligase to the ampicillin and sucrose based counter-selectable plasmid pCVD442. The plasmid pCVD442 is digested with the restriction enzyme, EcoRV, to generate the recombinant plasmid pCVD442-Δ1781.

Non-Polar Deletion for Generation of Mutant VC1781

The plasmid pCVD442-Δ1781 was introduced into *V. cholerae* O1 El Tor strain, CO 366 by bi-parental mating or conjugation on an LB agar plate. Four co-integrants, formed after conjugation of *V. cholerae* O1 El Tor strain CO-366 and *E. coli* harbouring the plasmid pCVD442-Δ1781, were purified by streaking one time under selection and then were passaged one time without selection to allow recombination to occur. Sixteen independent colonies were then streaked on the counter-selection medium—the LB medium containing ampicillin and polymixin B. The ampicillin and polymixin B resistant colonies were next streaked on LB medium without NaCl but containing 6% sucrose for sucrose-based selection.

The non-polar deletion mutants of vc1781 were confirmed by PCR assay. The strains were checked using the primers 1781UF and 1781DR. The sizes of the amplified products were 1.672 kb in the wild type strain and 949 bp in the mutants. The size of the ORF deleted in the mutants was 723 bp. The non-polar deletion mutants of vc1781 were denoted as SHVC1781.

Preparation of SHVC1782 (N-acetylmannosamine Kinase/ROK Kinase; VC1782)

Construction of Plasmid Vector pCVD442-Δ1782

A PCR assay with primers 1782UF (SEQ ID NO: 25) and 1782UR (SEQ ID NO: 26) were used for amplification of the region 379 bp upstream of the putative translational start site of vc1782 to obtain an amplified product of 379 bp. The primers 1782DF (SEQ ID NO: 27) and 1782DR (SEQ ID NO: 28) were used for the amplification of the region 433 bp downstream of vc1782 gene of the *V. cholerae* El Tor strain CO366, to obtain an amplified product of 433 bp.

A PCR assay comprising AmpliTaq polymerase PCR with primer pair 1782UF and 1782UR yielded amplified products of size 379 bp (upstream fragment) and with primer pair 1782DF and 1782DR yielded amplified products of size 433 bp (downstream fragment). For each set of PCR analysis, the reaction volume comprised the specific primers, genomic DNA, 10×PCR buffer with $Mgcl_2$, dNTPs mix and Taq DNA polymerase. The reaction volume was 25 μl. PCR parameters for amplifying upstream and downstream fragment are provided in Table 2. The amplified products were purified by two passages over the QiaQuick PCR purification kit (Qiagen Inc.) and used for the cross-over PCR assay.

Cross-Over PCR Assay

The primers 1782UR (SEQ ID NO: 26) and 1782DF (SEQ ID NO: 27) have 23 bp of overlapping nucleotide sequence, such that the crossover PCR brings the downstream region of vc1782 after stop codon to the upstream region before the start codon of vc1782.

The amplified upstream and downstream fragments were mixed in equimolar ratio and used for cross-over PCR with primers 1782UR (SEQ ID NO: 26) and 1782DF (SEQ ID NO: 27) to delete the ORF. For the cross-over PCR analysis, the reaction volume of 25 μl comprised the crossover primers, 10×PCR buffer with $Mgcl_2$, dNTPs mix and Taq DNA polymerase. The PCR parameters for the cross-over PCR assay is provided in Table 3.

The cross-over PCR assay yielded an amplified product of size 812 bp and was purified by two passages over the QiaQuick PCR purification kit (Qiagen Inc). The amplified and purified product of the cross-over PCR assay was then ligated using NEB T4DNA-ligase into the ampicillin and sucrose based counter-selectable plasmid pCVD442 and digested with EcoRV to generate the recombinant plasmid pCVD442-Δ1782.

Non-Polar Deletion for Generation of Mutant VC1782

The plasmid pCVD442-Δ1782 was introduced into *V. cholerae* O1 El Tor strain, CO 366 by bi-parental mating or conjugation on an LB agar plate. Four co-integrants, formed after conjugation of *V. cholerae* El Tor strain CO-366 and *E. coli* harbouring the plasmid pCVD442-Δ1782, were purified by streaking once under selection followed by passaging without selection to allow recombination to occur. Sixteen independent colonies were then streaked on the counter-selection medium—the LB medium containing ampicillin and polymixin B. The ampicillin and polymixin B resistant colonies were next streaked on LB medium without NaCl but containing 6% sucrose for sucrose-based selection. Best results were achieved when counter-selection plates were incubated at room temperature for 2 days.

The non-polar deletion mutants of vc1782 were confirmed by PCR assay. The strains were checked using the primers 1782UF and 1782DR. The sizes of the amplified products were 1.676 kb in wild type strain and 812 bp in the mutants.

The size of the ORF deleted in the mutants was 864 bp. The non-polar deletion mutants of vc1782 were denoted as SHVC1782.

Example 3

Preparation of SHNA1-A2 (Double Mutant of Deacetylase I nagA1 and Deacetylase II nagA2)

The mutant of *V. cholerae*, SHNA1 was used as the background strain. The plasmid pCVD442-ΔNA2 (of Example 2) was introduced into *V. cholerae* SHNA1 strain, by bi-parental mating or conjugation on an LB agar plate. Four co-integrants, formed after conjugation of SHNA1 and *E. coli* harbouring the plasmid pCVD442-ΔNA2, were purified by streaking once under selection and then passaged once without selection to allow recombination to occur. Sixteen independent colonies were then streaked on the counter-selection medium—the LB medium containing ampicillin and polymixin B. The ampicillin and polymixin B resistant colonies were next streaked on LB medium without NaCl but containing 6% sucrose for sucrose-based selection. Best results were achieved when counter-selection plates were incubated at room temperature for 2 days.

Colony lysis PCR assay using the primers NA2UF (SEQ ID NO: 9) and NA2DR (SEQ ID NO: 12) was carried out to check for gain of mutation. The single mutated strain gave an amplified product of 2.082 kb while the double mutated strain gave an amplified product of size 945 bp. The non-polar deletion mutants of nagA1-nagA2 were denoted as SHNA1-A2.

Example 4

Colonization Property of the Recombinant Strains of *Vibrio cholerae*

In-vitro Competition Assay

Wild type *V. cholerae* El Tor strain CO 366 strains were made lacZ negative. The mutant strains of SHNE, SHNB, SHNA1-A2 were each mixed with the wild-type *V. cholerae* in a ratio of 1:1 based on their optical densities and plated on LB streptomycin plates supplemented with 5-bromo-4-chloro-3-indolyl β-D-galactoside (X-gal) and incubated at 37° C., overnight. The viable colony forming units (CFU) were counted after the incubation period using the formula:

Competitive Index(CI)=CI of output/CI of input

CI of input or output=CFU of mutant/CFU of wild type

The in vitro competition index was almost 1 for the wild type and the three mutants of *V. cholerae*

In-vivo Infant Mouse Colonization Assay

To test the in-vivo colonization properties of the mutant strains, a mouse intestinal competition assay was carried out. Wild type *V. cholerae* El Tor strain CO 366 strains were made lacZ negative. 3-5 days old suckling mice were orogastrically challenged with a 100 μl mixture of wild type and mutant *V. cholerae* SHNA1-A2 strain mixed in a ratio of 1:1 based on their optical densities.

20 hours post challenge, the mice were sacrificed and their small intestines dissected, homogenized and plated on LB streptomycin plates supplemented with X-gal and incubated overnight at 37° C.

Viable CFU were counted for the in vivo competitive index. The competitive index was found to be 0.0001. FIG. 5A shows the results of the infant colonization studies for the mutants SHNB, SHNE and SHNA1-A2. The recovery rate of the mutant and wild type strains is given in Table 4.

Example 5

Estimation of Virulence Gene Transcripts in Recombinant Strains of *Vibrio cholerae*

RNA Extraction

Total RNA was isolated using TRIZOL Reagent following the standard protocol (Invitrogen, Carlsbad, Calif.). To the cell lysate 1 ml TRIZOL reagent was added and mixed well. After a 5-min incubation at 25° C., chloroform 200 μl was added and the tubes were vigorously vortexed for 15 s and incubated at room temperature for 2 min. The upper aqueous RNA-containing phase was collected following centrifugation at 12,000×g for 10 min at 4° C., into a fresh tube and then precipitated into pellet with isopropyl alcohol (~350 μl) by incubating for 10 min at room temperature and centrifuging 12,000×g for 10 min at 4° C. The RNA pellet was washed once with 1 ml 75% EtOH by centrifugation at 7500×g for 10 min at 4° C. The RNA pellet was dried in a vacuum concentrator (Concentrator Plus, Eppendorf) for 3 min and RNA was resuspended in RNase free water (Ambion, AM9939). RNA concentration and purity was determined at an optical density ratio of 260/280 using the Nanodrop® ND-1000 spectrophotometer (NanoDrop Technologies, Wilmington, Del.) and the integrity of total RNA was verified on an Agilent 2100 Bioanalyzer using the RNA 6000 Nano LabChip (Agilent Technologies). RNA was stored at −80° C. until further use.

RNA Quality Control

Total RNA integrity was assessed using RNA 6000 Nano Lab Chip on the 2100 Bioanalyzer (Agilent, Palo Alto, Calif.) following the manufacturer's protocol. Total RNA purity was assessed by the NanoDrop® ND-1000 UV-Vis Spectrophotometer (Nanodrop technologies, Rockland, USA). Total RNA with OD260/OD280>1.8 and OD260/OD230≥1.3 was used for microarray experiments. RNA was considered as good quality when the rRNA 28S/18S ratios were greater than or equal to 1.5, with the rRNA contribution being 30% or more and an RNA integrity number (RIN) was ≥7.0.

Estimation of Gene Expression

Total RNA from the wild type *V. cholerae* El Tor strain CO366 and the mutants (SHNB, SHNE, SHNA1-A2) was used for the study. 500 ng of DNase I (Invitrogen)-treated RNA was used for single-stranded cDNA synthesis in 10 μl of reaction mixture using a High-Capacity cDNA Reverse Transcription kit (Applied Biosystems). For qRT-PCR assays, the SYBR green PCR master mix was used. RT-PCR assays were carried out on an ABI Prism 7000 real-time PCR apparatus (Applied Biosystems).

The comparative CT method ($2^{-\Delta\Delta C_T}$) was used to determine the relative gene expression (Schmittgen, T. D., and Livak, K. J. (2008) Analyzing real-time PCR data by the comparative CTmethod *Nat. Protoc.* 3, 1101-1108).

Control reactions without reverse transcriptase were carried out for each cDNA preparation and ascertained that no amplification was obtained as judged by high CT (Murad, A. M., Lee, P. R., Broadbent, I. D., Barelle, C. J., and Brown, A. J. (2000) CIp10, anefficient and convenient integrating vector for *Candida albicans. Yeast* 16, 325-327), values and gel analysis. The qRT-PCR analyses revealed that while the expression of toxR, toxT and tcpA increased almost 1.5, 2 and ≥3 folds respectively in all the mutants, the levels of tcpP, tcpH, ctxA, ctxB and remained unaltered or decreased slightly (FIGS. 6A and 6B).

Detection of Cholera Toxin (CT) Using GM₁ ELISA

The wild type *V. cholerae* El Tor strain CO366 and the mutant strains, SHNA1-A2, SHNB and SHNE, were grown in AKI media at 30° C., overnight (OD 3.0) under constant shaking condition and an average of two independent assays was considered. Each assay was performed in duplicate. 20 µl cell free culture supernatants were added to wells of Microtitre plates coated with $GM_1$ (monosialoganglioside). The plates were subsequently treated with 1:100 diluted rabbit anti-CT antisera, anti-rabbit Ig peroxidase conjugate and developed with substrate solution containing 1 mg/ml O-phenelynediamine dihydrochloride and 0.12% $H_2O_2$. For each set known amount of purified CT were used to generate a standard curve from which the amount of CT in the test samples were calculated. CT produced was expressed as $\mu m l^{-1}$ per unit of optical density at 540 nm of bacterial cell suspension. As a negative control, *E. coli* was used. Average of two independent experiments was taken.

$GM_1$ ganglioside enzyme-linked Cholera Toxin (CT) assays showed that the production of CT was not significantly altered in the mutants when compared with the wild type (Table 6).

Example 6

Expression Analysis of Genes Regulated by nagC

The mutant SHNC and wild type *Vibrio cholerae* O1 El Tor strain CO366, were grown to log phase in M9-Glucose medium supplemented with amino-acids till early exponential phase at 30° C. (n=2 each strain), washed and induced in M9-Glucose (0.5%) or GlcNAc medium (0.5%) at 30° C. for 1 hour. Custom *Vibrio Cholera* 8×15 k array slides were used (AMADID: 22386). The probes were designed using the annotated genes in TIGR (cmr.jcvi.org) using N16961 (*Vibrio cholerae* O1 El Tor) as the reference strain. Probes were spotted in triplicates. NCBI protein coding sequence information was also taken into consideration.

Labelling and Microarray Hybridization

The RNA samples for gene expression were labelled using Agilent Quick Amp Kit PLUS (Part number: 5190-0444). 500 ng each of the samples were incubated with reverse trancription mix at 42° C. and converted to double stranded cDNA primed by oligodT with a T7 polymerase promoter. The cleaned up double stranded cDNA were used as template for aRNA generation. aRNA was generated by in vitro transcription and the dyes Cy3 CTP(Agilent) and Cy5 CTP(Agilent) were incorporated during this step. The cDNA synthesis and in vitro transcription steps were carried out at 40° C. Labelled aRNA was cleaned up and quality assessed for yields and specific activity.

Hybridization and Scanning

The labelled aRNA samples were hybridized on to a *Vibrio Cholera* Gene Expression Array 8×15K. 300 ng of Cy3 labelled and 300 ng of Cy5 labelled samples were fragmented and hybridized. Fragmentation of labelled aRNA and hybridization were done using the Gene Expression Hybridization kit of Agilent (Part Number 5188-5242). Hybridization was carried out in Agilent's Surehyb Chambers at 65° C. for 16 hours. The hybridized slides were washed using Agilent Gene Expression wash buffers (Part No: 5188-5327) and scanned using the Agilent Microarray Scanner G Model G2565BA at 5 micron resolution.

Hierarchical clustering analysis of microarray expression data for genes of the wild type *Vibrio cholerae* and SHNC mutant grown in the presence of glucose, showed that VC0994 (nagA1/Deacaetylase1), VC0995(nagE), and VCA1025 (nagB/Deaminase) were upregulated in the SHNC mutant (FIG. 5B). When SHNC mutant was grown in presence of GlcNAc, surprisingly there was a down regulation of genes viz. VC1776-VC1784 which included nagA2 and ROK kinase, due to the positive regulatory effect of NagC, as seen in Table 5. This transcriptome data indicates a more general role of NagC, and in particular, the significant role of NagC in the core intermediary metabolism as in gluconeogenesis, fatty acid metabolism, glycolysis, sialic acid degradation, etc.

TABLE 1

Primers used for the creation of mutants of the present invention

| Sl No | Primer name | SEQ ID NO | Primer Sequence | Product size |
|---|---|---|---|---|
| 1 | NA1UF | SEQ ID NO: 1 | 5'TTACCTAACTTTTGCGCATAT 3' | 503 bp |
| 2 | NA1UR | SEQ ID NO: 2 | 5'ACCAATCTGTCCGCCATTCATTAA ATCAGCTAATCCTCTTGTC 3' | |
| 3 | NA1DF | SEQ ID NO: 3 | 5'TAATGAATGGCGGACAGATTGGT 3' | 588 bp |
| 4 | NA1DR | SEQ ID NO: 4 | 5'TACCACGAACGTCGTTACCCA 3' | |
| 5 | NBUF | SEQ ID NO: 5 | 5'GTTACCACGCATGAAGAT 3' | 510 bp |
| 6 | NBUR | SEQ ID NO: 6 | 5'GTTTTTATTAGCTTGATTGAGATGT ATTGCCCTTAGATTTGAAT 3' | |
| 7 | NBDF | SEQ ID NO: 7 | 5'ATCTCAATCAAGCTAATAAAAAC 3' | 519 bp |
| 8 | NBDR | SEQ ID NO: 8 | 5'CCGTGCTGCTCACGGTAA 3' | |
| 9 | NA2UF | SEQ ID NO: 9 | 5'ATCATTGATGGCAAGCTTCAC 3' | 459 bp |
| 10 | NA2UR | SEQ ID NO: 10 | 5'AGGCATGTTTGATCGATAGCCGTTT ACTCCTTAAACTGAAATG 3' | |
| 11 | NA2DF | SEQ ID NO: 11 | 5'GCTATCGATCAAACATGCC 3' | 486 bp |
| 12 | NA2DR | SEQ ID NO: 12 | 5'GCTTGTCGCCATACCGAAC 3' | |
| 13 | NCUF | SEQ ID NO: 13 | 5'CTGAACATATTGAGAAGCTGG 3' | 616 bp |
| 14 | NCUR | SEQ ID NO: 14 | 5'TTGCGTAAGCTTAACTAAAAAGCT ATCAATTCTGCTCGTATTG 3' | |
| 15 | NCDF | SEQ ID NO: 15 | 5'GCTTTTTAGTTAAGCTTACGCAA 3' | 432 bp |
| 16 | NCDR | SEQ ID NO: 16 | 5'ATGAGTTTATCAAAAGAAAG 3' | |

TABLE 1-continued

Primers used for the creation of mutants of the present invention

| Sl No | Primer name | SEQ ID NO | Primer Sequence | Product size |
|---|---|---|---|---|
| 17 | NEUF | SEQ ID NO: 17 | 5'GCCTGTGTAGATTTTGCAG 3' | 505 bp |
| 18 | NEUR | SEQ ID NO: 18 | 5'AGGCTAGGGTTTAAACTCGACTTAAGTTCCCCCTATAGGAT 3' | |
| 19 | NEDF | SEQ ID NO: 19 | 5'TCGAGTTTAAACCCTAGCCTGA 3' | 577 bp |
| 20 | NEDR | SEQ ID NO: 20 | 5'CGTATTCATACAACTTGTCAAAA 3' | |
| 21 | 1781UF | SEQ ID NO: 21 | 5'AGCATAAGTTATATCGAGATC 3' | 475 bp |
| 22 | 1781UR | SEQ ID NO: 22 | 5'TCCGCCGATATCGATTTTTCTTTTCTAAAAACG 3' | |
| 23 | 1781DF | SEQ ID NO: 23 | 5'CCATCGATATCGGCGGAAC 3' | 474 bp |
| 24 | 1781DR | SEQ ID NO: 24 | 5'ACCTTCAATGGCCACCGAC 3' | |
| 25 | 1782UF | SEQ ID NO: 25 | 5'TCGAATCACTCCTTTTGTTTC 3' | 379 bp |
| 26 | 1782UR | SEQ ID NO: 26 | 5'ATTGCCTTTAATGCCATCGTTTCCTTTCTCCCGCAGCTT 3' | |
| 27 | 1782DF | SEQ ID NO: 27 | 5'ACGATGGCATTAAAGGCAATT 3' | 433 bp |
| 28 | 1782DR | SEQ ID NO: 28 | 5'ATAGAACAGATCTGGGTTATG 3' | |

TABLE 2

Run protocol for conventional PCR assay

| Sl No. | Description | Temperature | Time | Cycles |
|---|---|---|---|---|
| 1. | Initial Denaturation | 94° C. | 5 mins | |
| 2 | Denaturation | 94° C. | 2 mins | 29 Cycles |
| 3 | Annealing | 55° C. | 45 secs | |
| 4 | Extension | 72° C. | 45 secs | |
| 5 | Final extension | 72° C. | 10 mins | |

TABLE 3

Run protocol for Cross over PCR assay

| Sl No. | Description | Temperature | Time | Cycles |
|---|---|---|---|---|
| 1. | Initial Denaturation | 94° C. | 5 mins | |
| 2 | Denaturation | 94° C. | 2 mins | 5 Cycles |
| 3 | Annealing | 50° C. | 45 secs | |
| 4 | Extension | 72° C. | 1 min | |
| 5 | Denaturation | 94° C. | 2 mins | 29 cycles |
| 6 | Annealing | 55° C. | 45 secs | |
| 7 | Extension | 72° C. | 1 min | |
| 8 | Final extension | 72° C. | 10 mins | |

TABLE 4

Recovery rate of wild type and SHNA1-A2 mutant strains of *V. cholerae* in mice small intestinal homogenates. White colonies represent wild type, blue colonies represent the mutant. (TNTC: Too numerous to count).

| Tube dilution | Plating dilution | Average CFU/ml |
|---|---|---|
| $10^{-3}$ | $10^{-4}$ | Set1: TNTC |
| | | Set2: TNTC |
| | | Set3: TNTC |
| $10^{-4}$ | $10^{-5}$ | Set1: White = 477; Blue = 0 |
| | | Set2: White = 438; Blue = 2 |
| | | Set3: White: 464; Blue = 1 |
| $10^{-5}$ | $10^{-6}$ | Set1: White = 53; Blue = Nil |
| | | Set2: White = 59; Blue = Nil |
| | | Set3: White = 48; Blue = Nil |

TABLE 5

List of genes down-regulated in nagC mutant in the presence of GlcNAc

| Gene | Fold change | Biological function |
|---|---|---|
| VC0620 | 3.25 | ABC-transporter, periplasmic peptide binding protein (Putative GlcNAc transporter) |
| VC0298 | 2.89 | Acetyl Co-A synthase |
| VC1781 | 3.21 | Epimerase (Putative ManNAc-6-p 2-epimerase) |
| VC1782 | 2.82 | ROK kinase (Putative ManNAc kinase) |
| VC1783 | 2.76 | GlcNAc-6-phosphate deacetylase 2 (Nag A2) |
| VC0972 | 2.65 | Porin, putative |
| VC2698 | 2.62 | Alanine/aspartate metabolism |
| VC1776 | 2.41 | N-acetylneuraminic acid lyase (nanA) |
| VC1779 | 4.05 | TripartoteATP-independent periplasmic transporter |
| VC1778 | 2.45 | TRAP transporter |
| VC1777 | 2.42 | TRAP transporter |
| VC2738 | 2.00 | Gluconeogenesis |
| VC1741 | 2.14 | TetR family transcriptional regulator |
| VC2704 | 2.13 | Hypothetical protein |
| VC2758 | 2.13 | FadB (fattyacid metabolism) |
| VC2759 | 2.08 | FadR (fattyacid metabolism) |
| VC0730 | 2.02 | Copper homeostasis (cutC) |
| VCA0052 | 2.0 | Hypothetical protein |
| VC1784 | 1.99 | Neuraminidase (nanH) |
| VC0728 | 1.99 | Conserved hypothetical protein |
| VC1774 | 1.6 | Conserved hypothetical protein |

TABLE 6

CT production by *V. cholerae* El Tor strain CO366 and its recombinant strains, SHNA1-A2 and SHNB, grown in AKI medium at 30° C. for 16 h and assayed by $GM_1$ ELISA method.

| Strains | Amount of CT (ng/ml/opacity unit at 540 nm) produced | |
|---|---|---|
| | Set I | Set II |
| Wild type *V. cholerae* | 83.2 | 136.5 |
| SHNA1-A2 mutant | 111.0 | 95.4 |
| SHNB mutant | 81.0 | 72.5 |
| *E. coli* (DH5α) | <0.001 | <0.001 |

What is claimed is:

1. A recombinant strain of *Vibrio cholerae* incapable of utilizing N-acetylglucosamine (GlcNAc), wherein said recombinant strain comprises at least one mutation in at least one of the genes selected from the group consisting of N-acetylglucosamine-6-phosphate deacetylase (nagA1), N-acetylglucosamine-6-phosphate deacetylase II (nagA2), glucosamine 6-phosphate deaminase/isomerase (nagB), and GlcNAc specific transporter (nagE), wherein said recombinant strain shows impaired colonization in a host as compared to a wild type *Vibrio cholerae.*

2. The recombinant strain of *Vibrio cholerae* according to claim 1, wherein the mutation is selected from a group consisting of deletion, addition, and substitution.

3. The recombinant strain of *Vibrio cholerae* according to claim 2, wherein the mutation is a non-polar deletion.

4. The recombinant strain of *Vibrio cholerae* according to claim 1, wherein the host is an animal or a human.

5. The recombinant strain of *Vibrio cholerae* according to claim 1, wherein the wild-type *Vibrio cholerae* is *Vibrio cholerae* El Tor strain CO366.

6. A composition comprising the recombinant strain of *Vibrio cholerae* according to claim 1.

7. A vaccine comprising the recombinant strain of *Vibrio cholerae* according to claim 1.

8. The composition according to claim 6, wherein the composition optionally comprises a pharmaceutically acceptable carrier, diluent, adjuvant, and/or additive.

9. The vaccine according to claim 7, wherein the vaccine optionally comprises a pharmaceutically acceptable carrier, diluent, adjuvant, and/or additive.

10. The recombinant strain of *Vibrio cholera* according to claim 1, wherein the at least one mutation is a null mutation.

11. The recombinant strain of *Vibrio cholera* according to claim 10, wherein said recombinant strain comprises at least one mutation in the nagA1 gene and at least one mutation in the nagA2 gene.

12. The recombinant strain of *Vibrio cholera* according to claim 10, wherein said recombinant strain comprises at least one mutation in the nagB gene.

13. The recombinant strain of *Vibrio cholera* according to claim 10, wherein said recombinant strain comprises at least one mutation in the nagE gene.

* * * * *

UNITED STATES PATENT AND TRADEMARK OFFICE
CERTIFICATE OF CORRECTION

PATENT NO. : 8,734,814 B2
APPLICATION NO. : 13/451481
DATED : May 27, 2014
INVENTOR(S) : Asis Datta et al.

Page 1 of 1

It is certified that error appears in the above-identified patent and that said Letters Patent is hereby corrected as shown below:

Title page,

ADD

--(73) Assignee: National Institute of Plant Genome Research Organization, New Deli (IN)--.

In the Claims,

In Claim 10, at Column 34, line 35,
delete "cholera"
and replace it with --cholerae--.

In Claim 11, at Column 34, line 37,
delete "cholera"
and replace it with --cholerae--.

In Claim 12, at Column 34, line 41,
delete "cholera"
and replace it with --cholerae--.

In Claim 13, at Column 34, line 44,
delete "cholera"
and replace it with --cholerae--.

Signed and Sealed this
Ninth Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,734,814 B2
APPLICATION NO. : 13/451481
DATED : May 27, 2014
INVENTOR(S) : Asis Datta et al.

It is certified that error appears in the above-identified patent and that said Letters Patent is hereby corrected as shown below:

Title Page,
Item [73], Assignee, "National Institute of Plant Genome Research Organization, New Deli (IN)" (as inserted on title page of patent in the Certificate of Correction issued September 9, 2014) is deleted and patent is returned to its original state where there is no assignee displayed on the title page of patent.

Signed and Sealed this
Thirtieth Day of September, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,734,814 B2 | Page 1 of 1 |
| APPLICATION NO. | : 13/451481 | |
| DATED | : May 27, 2014 | |
| INVENTOR(S) | : Asis Datta et al. | |

It is certified that error appears in the above-identified patent and that said Letters Patent is hereby corrected as shown below:

Title page, "item (76)" should read --item (75)--

Title page,

ADD

--(73) Assignee: National Institute of Plant Genome Research Organization, New Deli (IN)--

Signed and Sealed this
Nineteenth Day of May, 2015

Michelle K. Lee
*Director of the United States Patent and Trademark Office*

SEQUENCE LISTING

```
<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<223> OTHER INFORMATION: Forward Primer

<400> SEQUENCE: 1
ttacctaact tttgcgcata t                                              21

<210> SEQ ID NO 2
<211> LENGTH: 43
<212> TYPE: DNA
<213> ORGANISM: Artificial sequence
<220> FEATURE:
<223> OTHER INFORMATION: Reverse Primer

<400> SEQUENCE: 2
accaatctgt ccgccattca ttaaatcagc taatcctctt gtc                      43

<210> SEQ ID NO 3
<211> LENGTH: 23
<212> TYPE: DNA
<213> ORGANISM: Artificial Sequence
<220> FEATURE:
<223> OTHER INFORMATION: Forward Primer

<400> SEQUENCE: 3
taatgaatgg cggacagatt ggt                                            23

<210> SEQ ID NO 4
<211> LENGTH: 21
<212> TYPE: DNA
<213> ORGANISM: Artificial Sequence
<220> FEATURE:
<223> OTHER INFORMATION: Reverse Primer

<400> SEQUENCE: 4
taccacgaac gtcgttaccc a                                              21

<210> SEQ ID NO 5
<211> LENGTH: 18
<212> TYPE: DNA
<213> ORGANISM: Artificial Sequence
<220> FEATURE:
<223> OTHER INFORMATION: Forward Primer

<400> SEQUENCE: 5
gttaccacgc atgaagat                                                  18

<210> SEQ ID NO 6
<211> LENGTH: 44
<212> TYPE: DNA
<213> ORGANISM: Artificial sequence
<220> FEATURE:
<223> OTHER INFORMATION: Reverse Primer

<400> SEQUENCE: 6
gtttttatta gcttgattga gatgtattgc ccttagattt gaat                     44
```

```
<210> SEQ ID NO 7
<211> LENGTH: 23
<212> TYPE: DNA
<213> ORGANISM: Artificial Sequence
<220> FEATURE:
<223> OTHER INFORMATION: Forward Primer

<400> SEQUENCE: 7
atctcaatca agctaataaa aac                                              23

<210> SEQ ID NO 8
<211> LENGTH: 18
<212> TYPE: DNA
<213> ORGANISM: Artificial Sequence
<220> FEATURE:
<223> OTHER INFORMATION: Reverse Primer

<400> SEQUENCE: 8
ccgtgctgct cacggtaa                                                    18

<210> SEQ ID NO 9
<211> LENGTH: 21
<212> TYPE: DNA
<213> ORGANISM: Artificial Sequence
<220> FEATURE:
<223> OTHER INFORMATION: Forward Primer

<400> SEQUENCE: 9
atcattgatg gcaagcttca c                                                21

<210> SEQ ID NO 10
<211> LENGTH: 43
<212> TYPE: DNA
<213> ORGANISM: Artificial sequence
<220> FEATURE:
<223> OTHER INFORMATION: Reverse Primer

<400> SEQUENCE: 10
aggcatgttt gatcgatagc cgtttactcc ttaaactgaa atg                        43

<210> SEQ ID NO 11
<211> LENGTH: 19
<212> TYPE: DNA
<213> ORGANISM: Artificial Sequence
<220> FEATURE:
<223> OTHER INFORMATION: Forward Primer

<400> SEQUENCE: 11
gctatcgatc aaacatgcc                                                   19

<210> SEQ ID NO 12
<211> LENGTH: 19
<212> TYPE: DNA
<213> ORGANISM: Artificial Sequence
<220> FEATURE:
<223> OTHER INFORMATION: Reverse Primer

<400> SEQUENCE: 12
gcttgtcgcc ataccgaac                                                   19

<210> SEQ ID NO 13
<211> LENGTH: 21
<212> TYPE: DNA
<213> ORGANISM: Artificial Sequence
<220> FEATURE:
<223> OTHER INFORMATION: Forward Primer
```

<400> SEQUENCE: 13
ctgaacatat tgagaagctg g                                          21

<210> SEQ ID NO 14
<211> LENGTH: 43
<212> TYPE: DNA
<213> ORGANISM: Artificial Sequence
<220> FEATURE:
<223> OTHER INFORMATION: Reverse Primer

<400> SEQUENCE: 14
ttgcgtaagc ttaactaaaa agctatcaat tctgctcgta ttg                  43

<210> SEQ ID NO 15
<211> LENGTH: 23
<212> TYPE: DNA
<213> ORGANISM: Artificial Sequence
<220> FEATURE:
<223> OTHER INFORMATION: Forward Primer

<400> SEQUENCE: 15 gcttttagt taagcttacg caa                                         23

<210> SEQ ID NO 16
<211> LENGTH: 20
<212> TYPE: DNA
<213> ORGANISM: Artificial Sequence
<220> FEATURE:
<223> OTHER INFORMATION: Reverse Primer

<400> SEQUENCE: 16
atgagtttat caaaagaaag                                            20

<210> SEQ ID NO 17
<211> LENGTH: 19
<212> TYPE: DNA
<213> ORGANISM: Artificial Sequence
<220> FEATURE:
<223> OTHER INFORMATION: Forward Primer

<400> SEQUENCE: 17
gcctgtgtag attttgcag                                             19

<210> SEQ ID NO 18
<211> LENGTH: 41
<212> TYPE: DNA
<213> ORGANISM: Artificial sequence
<220> FEATURE:
<223> OTHER INFORMATION: Reverse Primer

<400> SEQUENCE: 18
aggctagggt ttaaactcga cttaagttcc ccctatagga t                    41

<210> SEQ ID NO 19
<211> LENGTH: 22
<212> TYPE: DNA
<213> ORGANISM: Artificial Sequence
<220> FEATURE:
<223> OTHER INFORMATION: Forward Primer

<400> SEQUENCE: 19
tcgagtttaa accctagcct ga                                         22

<210> SEQ ID NO 20
<211> LENGTH: 23
<212> TYPE: DNA
<213> ORGANISM: Artificial Sequence
<220> FEATURE:
<223> OTHER INFORMATION: Reverse Primer

<400> SEQUENCE: 20
cgtattcata caacttgtca aaa                                          23

<210> SEQ ID NO 21
<211> LENGTH: 21
<212> TYPE: DNA
<213> ORGANISM: Artificial Sequence
<220> FEATURE:
<223> OTHER INFORMATION: Forward Primer

<400> SEQUENCE: 21
agcataagtt atatcgagat c                                            21

<210> SEQ ID NO 22
<211> LENGTH: 33
<212> TYPE: DNA
<213> ORGANISM: Artificial Sequence
<220> FEATURE:
<223> OTHER INFORMATION: Reverse Primer

<400> SEQUENCE: 22
tccgccgata tcgatttttc ttttctaaaa acg                               33

<210> SEQ ID NO 23
<211> LENGTH: 19
<212> TYPE: DNA
<213> ORGANISM: Artificial Sequence
<220> FEATURE:
<223> OTHER INFORMATION: Forward Primer

<400> SEQUENCE: 23
ccatcgatat cggcggaac                                               19

<210> SEQ ID NO 24
<211> LENGTH: 19
<212> TYPE: DNA
<213> ORGANISM: Artificial Sequence
<220> FEATURE:
<223> OTHER INFORMATION: Reverse Primer

<400> SEQUENCE: 24
accttcaatg gccaccgac                                               19

<210> SEQ ID NO 25
<211> LENGTH: 21
<212> TYPE: DNA
<213> ORGANISM: Artificial Sequence
<220> FEATURE:
<223> OTHER INFORMATION: Forward Primer

<400> SEQUENCE: 25
tcgaatcact cctttgttt c                                             21

<210> SEQ ID NO 26
<211> LENGTH: 39
<212> TYPE: DNA
<213> ORGANISM: Artificial Sequence
<220> FEATURE:
<223> OTHER INFORMATION: Reverse Primer

```
<400> SEQUENCE: 26
attgccttta atgccatcgt ttcctttctc ccgcagctt                                39

<210> SEQ ID NO 27
<211> LENGTH: 21
<212> TYPE: DNA
<213> ORGANISM: Artificial Sequence
<220> FEATURE:
<223> OTHER INFORMATION: Forward Primer

<400> SEQUENCE: 27
acgatggcat taaaggcaat t                                                  21

<210> SEQ ID NO 28
<211> LENGTH: 21
<212> TYPE: DNA
<213> ORGANISM: Artificial sequence
<220> FEATURE:
<223> OTHER INFORMATION: Reverse Primer

<400> SEQUENCE: 28
atagaacaga tctgggttat g                                                  21
```